(12) United States Patent
Zubiate et al.

(10) Patent No.: US 8,397,481 B2
(45) Date of Patent: Mar. 19, 2013

(54) STEERABLE MULTI-LINKED DEVICE HAVING A MODULAR LINK ASSEMBLY

(75) Inventors: Brett Zubiate, Pittsburgh, PA (US); Howard Choset, Pittsburgh, PA (US); Amir Degani, Pittsburgh, PA (US); Michael Schwerin, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 0 days.

(21) Appl. No.: 13/353,971

(22) Filed: Jan. 19, 2012

(65) Prior Publication Data

US 2012/0180591 A1    Jul. 19, 2012

Related U.S. Application Data

(63) Continuation of application No. 12/943,669, filed on Nov. 10, 2010, now Pat. No. 8,099,939, which is a continuation of application No. 11/923,246, filed on Oct. 24, 2007, now Pat. No. 7,854,109.

(60) Provisional application No. 60/862,636, filed on Oct. 24, 2006.

(51) Int. Cl.
*A61B 1/32* (2006.01)
*A61B 1/00* (2006.01)
*F16G 13/16* (2006.01)

(52) U.S. Cl. ........... 59/78.1; 248/49; 600/114; 600/144; 600/201; 600/206; 604/524; 607/122; 607/125

(58) Field of Classification Search ............. 59/78.1; 248/49; 600/114, 144, 149, 201, 528, 585; 604/524; 607/122, 125
See application file for complete search history.

(56) References Cited

U.S. PATENT DOCUMENTS

| | | |
|---|---|---|
| 3,060,972 A | 10/1962 | Sheldon |
| 3,643,653 A | 2/1972 | Takahashi et al. |
| 4,805,477 A | 2/1989 | Akeel |
| 4,830,569 A | 5/1989 | Jannborg |
| 4,941,457 A | 7/1990 | Hasegawa |
| 5,142,932 A | 9/1992 | Moya et al. |
| 5,143,475 A | 9/1992 | Chikama |
| 5,251,611 A | 10/1993 | Zehel et al. |
| 5,318,526 A | 6/1994 | Cohen |
| 5,327,905 A | 7/1994 | Avitall |
| 5,386,741 A | 2/1995 | Rennex |
| 5,467,763 A | 11/1995 | McMahon et al. |
| 5,472,017 A | 12/1995 | Kovalcheck |
| 5,483,951 A | 1/1996 | Frassica et al. |
| 5,514,157 A | 5/1996 | Nicholas et al. |
| 5,531,715 A | 7/1996 | Engelson et al. |
| 5,549,542 A | 8/1996 | Kovalcheck |
| 5,605,543 A | 2/1997 | Swanson |
| 5,634,466 A | 6/1997 | Gruner |
| 5,662,587 A | 9/1997 | Grundfest et al. |
| 5,743,876 A | 4/1998 | Swanson |
| 5,759,151 A | 6/1998 | Sturges |
| 5,836,199 A | 11/1998 | Loud |
| 6,036,677 A | 3/2000 | Javier, Jr. et al. |
| 6,197,017 B1 | 3/2001 | Brock et al. |
| 6,221,061 B1 | 4/2001 | Engelson et al. |
| 6,432,112 B2 | 8/2002 | Brock et al. |
| 6,491,681 B1 * | 12/2002 | Kunis et al. ................. 604/528 |
| 6,517,477 B1 | 2/2003 | Wendlandt |

(Continued)

FOREIGN PATENT DOCUMENTS

WO        2006083306 A2      8/2006

*Primary Examiner* — David B Jones
(74) *Attorney, Agent, or Firm* — Fox Rothschild LLP

(57) ABSTRACT

A steerable multi-linked device. The device includes a first multi-linked mechanism and a second multi-linked mechanism. At least one of the first and second multi-linked mechanisms is steerable and includes a modular link assembly at an end thereof. The modular link assembly includes a base, and a tip removably connected to the base.

20 Claims, 36 Drawing Sheets

U.S. PATENT DOCUMENTS

| | | | |
|---|---|---|---|
| 6,554,844 B2 | 4/2003 | Lee et al. |
| 6,610,007 B2 | 8/2003 | Belson et al. |
| 6,623,448 B2 | 9/2003 | Slater |
| 6,638,266 B2 | 10/2003 | Wilson et al. |
| 6,682,493 B2 | 1/2004 | Mirigian |
| 6,692,485 B1 | 2/2004 | Brock et al. |
| 6,697,048 B2 | 2/2004 | Rosenberg et al. |
| 6,730,020 B2 | 5/2004 | Peng et al. |
| 6,790,173 B2 | 9/2004 | Saadat et al. |
| 6,800,056 B2 | 10/2004 | Tartaglia et al. |
| 6,827,710 B1 | 12/2004 | Mooney et al. |
| 6,837,846 B2 | 1/2005 | Jaffe et al. |
| 6,837,847 B2 | 1/2005 | Ewers et al. |
| 6,858,005 B2 | 2/2005 | Ohline et al. |
| 6,869,396 B2 | 3/2005 | Belson |
| 6,890,297 B2 | 5/2005 | Belson |
| 6,899,673 B2 | 5/2005 | Ogura et al. |
| 6,907,298 B2 | 6/2005 | Smits et al. |
| 6,960,162 B2 | 11/2005 | Saadat et al. |
| 6,960,163 B2 | 11/2005 | Ewers et al. |
| 6,963,792 B1 | 11/2005 | Green |
| 6,974,411 B2 | 12/2005 | Belson |
| 6,976,991 B2 | 12/2005 | Hebert et al. |
| 6,984,203 B2 | 1/2006 | Tartaglia et al. |
| 7,029,435 B2 | 4/2006 | Nakao |
| 7,041,052 B2 | 5/2006 | Saadat et al. |
| 7,044,907 B2 | 5/2006 | Belson |
| 7,087,013 B2 | 8/2006 | Belson et al. |
| 7,090,637 B2 | 8/2006 | Danitz et al. |
| 7,090,683 B2 | 8/2006 | Brock et al. |
| 7,108,688 B2 | 9/2006 | Jensen |
| 7,128,708 B2 | 10/2006 | Saadat et al. |
| 7,169,141 B2 | 1/2007 | Brock et al. |
| 7,171,279 B2 | 1/2007 | Buckingham et al. |
| 7,182,731 B2 | 2/2007 | Nguyen et al. |
| 7,214,230 B2 | 5/2007 | Brock et al. |
| 7,232,434 B2 | 6/2007 | Suyama et al. |
| 7,250,027 B2 | 7/2007 | Barry |
| 7,278,253 B2 | 10/2007 | Wehler et al. |
| 7,322,935 B2 | 1/2008 | Palmer et al. |
| 7,338,505 B2 | 3/2008 | Belson |
| 7,484,351 B2 | 2/2009 | Harada et al. |
| 7,854,109 B2 * | 12/2010 | Zubiate et al. ............ 59/78.1 |
| 8,099,939 B2 * | 1/2012 | Zubiate et al. ............ 59/78.1 |
| 2005/0240078 A1 | 10/2005 | Kwon et al. |

* cited by examiner

STEERABLE MULTI-LINKED DEVICE HAVING A MODULAR LINK ASSEMBLY

CROSS-REFERENCE TO RELATED APPLICATION

This application claims priority to, and is a continuation of U.S. patent application Ser. No. 12/943,669, filed on Nov. 10, 2010, which claims priority to, and is a continuation of U.S. patent application Ser. No. 11/923,246, filed on Oct. 24, 2007, which claims priority to U.S. patent application Ser. No. 60/862,636, filed on Oct. 24, 2006, the disclosures of which are incorporated herein by reference in their entireties.

Not applicable

BACKGROUND

This application discloses an invention that is related, generally and in various embodiments, to a modular link assembly for a multi-linked device.

There are many types of steerable multi-linked devices, and such devices are utilized in a variety of different applications. In general, the steerable end of such devices is a fixed component which limits the versatility of the device. For example, the fixed component at the steerable end of a given multi-linked device may render the device suitable for only a single specific application.

SUMMARY

In one general respect, this application discloses a steerable multi-linked device. According to various embodiments, the device includes a first multi-linked mechanism and a second multi-linked mechanism. At least one of the first and second multi-linked mechanisms is steerable and includes a modular link assembly at an end thereof. The modular link assembly includes a base, and a tip removably connected to the base.

DESCRIPTION OF DRAWINGS

Various embodiments of the invention are described herein by way of example in conjunction with the following figures.

DETAILED DESCRIPTION

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

According to various embodiments, the modular link assembly may be utilized as an end link of a variety of different multi-link devices. For example, the modular link assembly may be utilized as an end link on a multi-linked device such as the steerable multi-linked device described in FIGS. 1-11. For ease of explanation purposes, the modular link assembly will be described in the context of its use with various embodiments of the steerable multi-linked device described in FIGS. 1-11. However, one skilled in the art will appreciate that the modular link assembly may be utilized with other types of multi-linked devices.

Figure 1A:
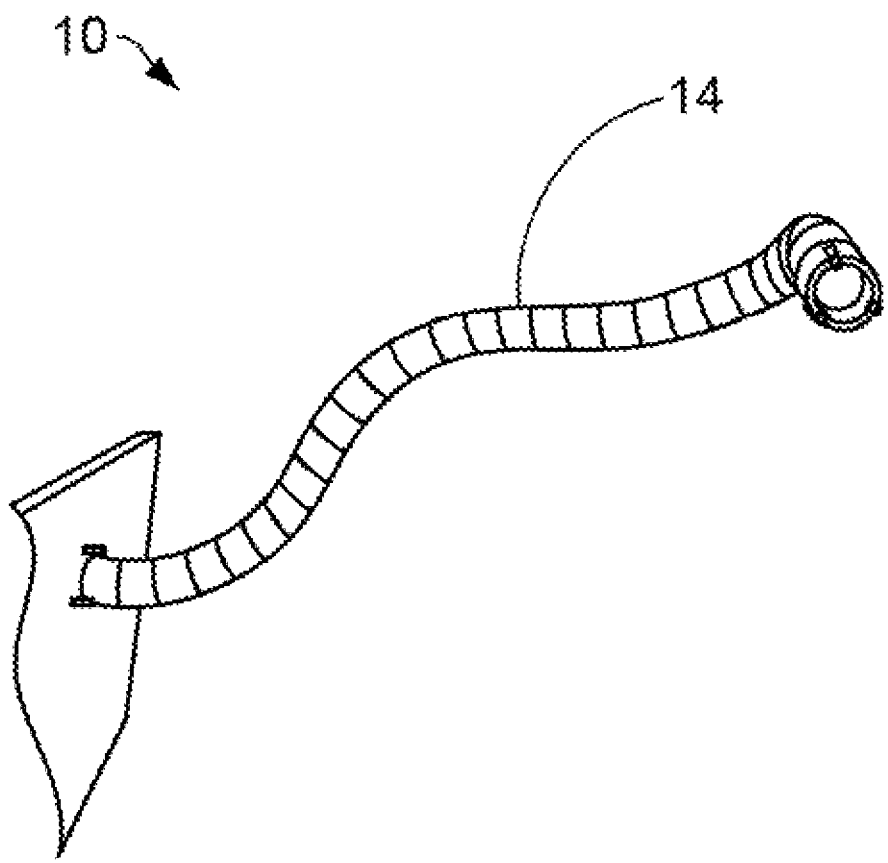
FIGS. 1A and 1B illustrate various embodiments of a steerable multi-linked device.
Figure 1B:
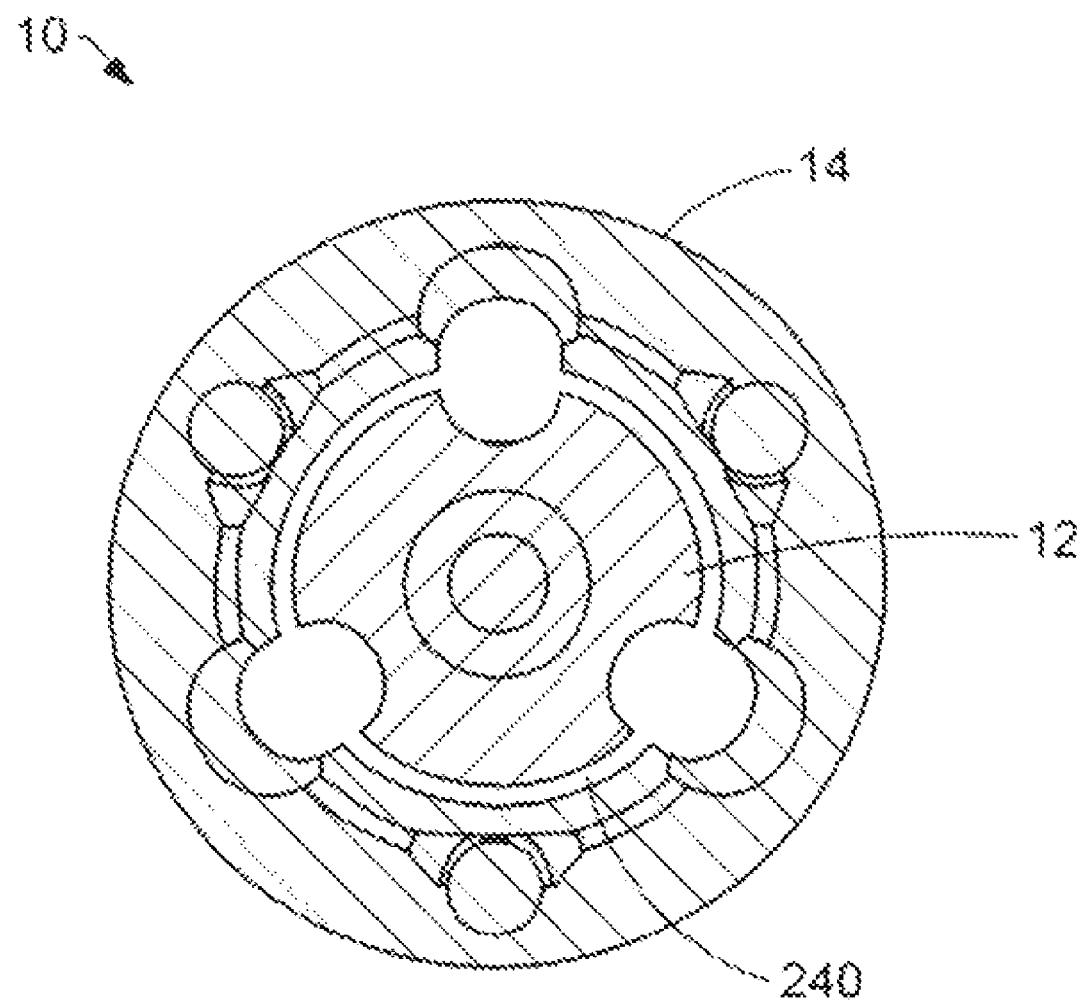

FIGS. 1A and 1B illustrate various embodiments of a steerable multi-linked device 10. Various embodiments of the device 10 may be utilized for medical procedures (e.g., minimally invasive procedures), for surveillance applications, for inspection applications, for search and rescue applications, etc. For purposes of clarity only, the utility of the device 10 will be described hereinbelow in the context of its applicability to medical procedures. However, a person skilled in the art will appreciate that the device 10 can be utilized in a variety of different applications.

The device 10 includes a first mechanism 12 and a second mechanism 14. According to various embodiments, the second mechanism 14 is structured and arranged to receive and surround the first mechanism 12 as shown in FIG. 1B. For such embodiments, the first mechanism 12 may be considered the inner mechanism or the core mechanism, and the second mechanism 14 may be considered the outer mechanism or the sleeve mechanism. According to other embodiments, the first and second mechanisms 12, 14 may be structured and arranged to have a relationship other than a concentric relationship. For example, one skilled in the art will appreciate that, according to various embodiments, the first and second mechanisms 12, 14 may be structured and arranged to operate in a side-by-side arrangement, where the first mechanism 12 operates adjacent to the second mechanism 14. As described in more detail hereinbelow, the first mechanism 12 may operate in either a rigid mode or a limp mode, the second mechanism 14 may operate in either a rigid mode or a limp mode, and the first and second mechanisms 12, 14 may operate independent of one another. Both the first mechanism 12 and the second mechanism 14 may be steerable mechanisms. Accordingly, it will be appreciated that the device 10 may be utilized to navigate a luminal space as well as any three-dimensional path within an interactivity space. The device 10 may also include a first cable 16, a second cable 18, a third cable 20, and a fourth cable 22. The first, second and third cables 16, 18, 20 may be considered steering cables, and the fourth cable 22 may be considered a tensioning cable.

Figure 2:
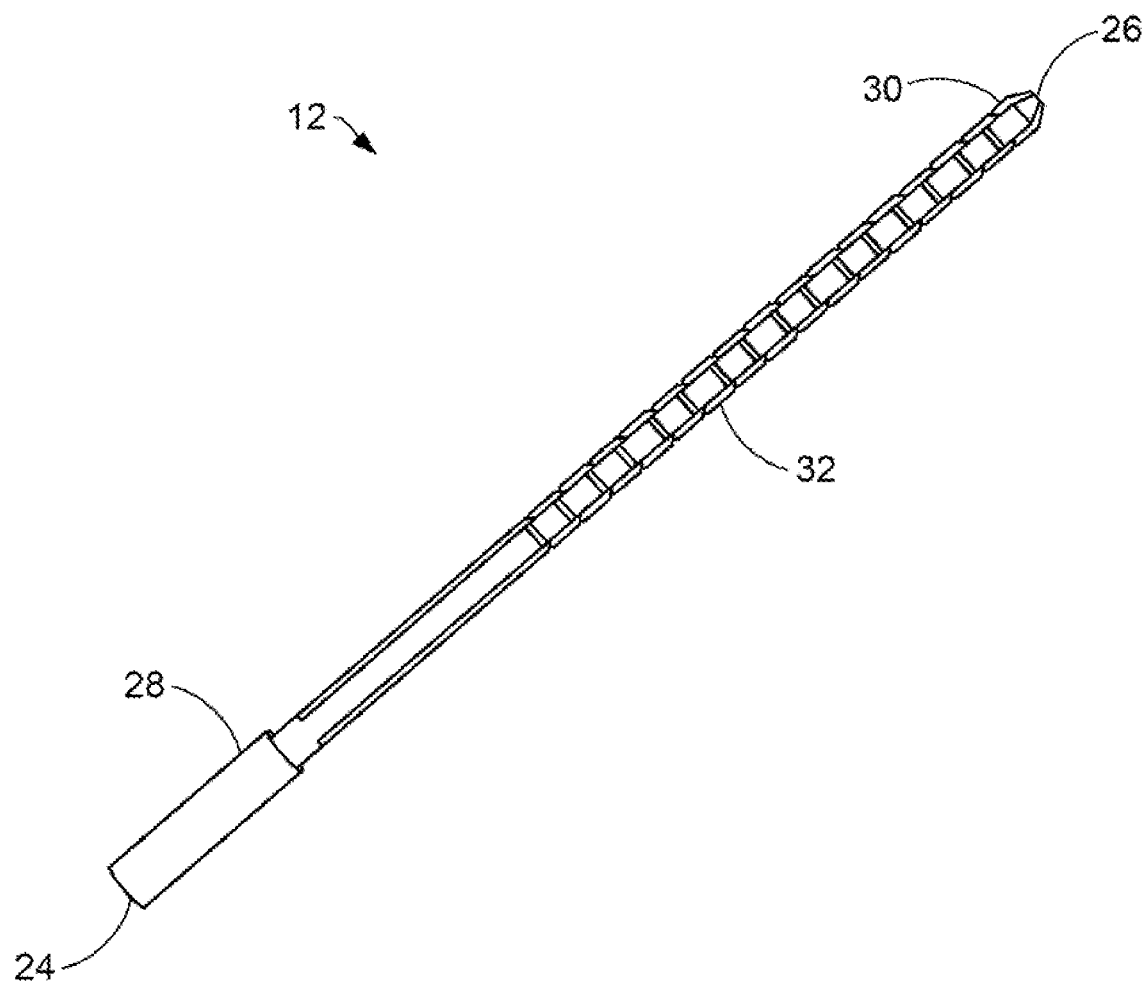
FIG. 2 illustrates various embodiments of a core mechanism of the device of FIG. 1.

FIG. 2 illustrates various embodiments of the first mechanism 12 of the device 10. The first mechanism 12 is a multi-linked mechanism and includes a first end 24 and a second end 26. The first end 24 may be considered the proximal end and the second end 26 may be considered the distal end. The first mechanism 12 includes a first link 28, a second link 30, and any number of intermediate links 32 between the first and second links 28, 30. The first link 28 may be considered the proximal link, and the second link 30 may be considered the distal link.

Figure 3A:
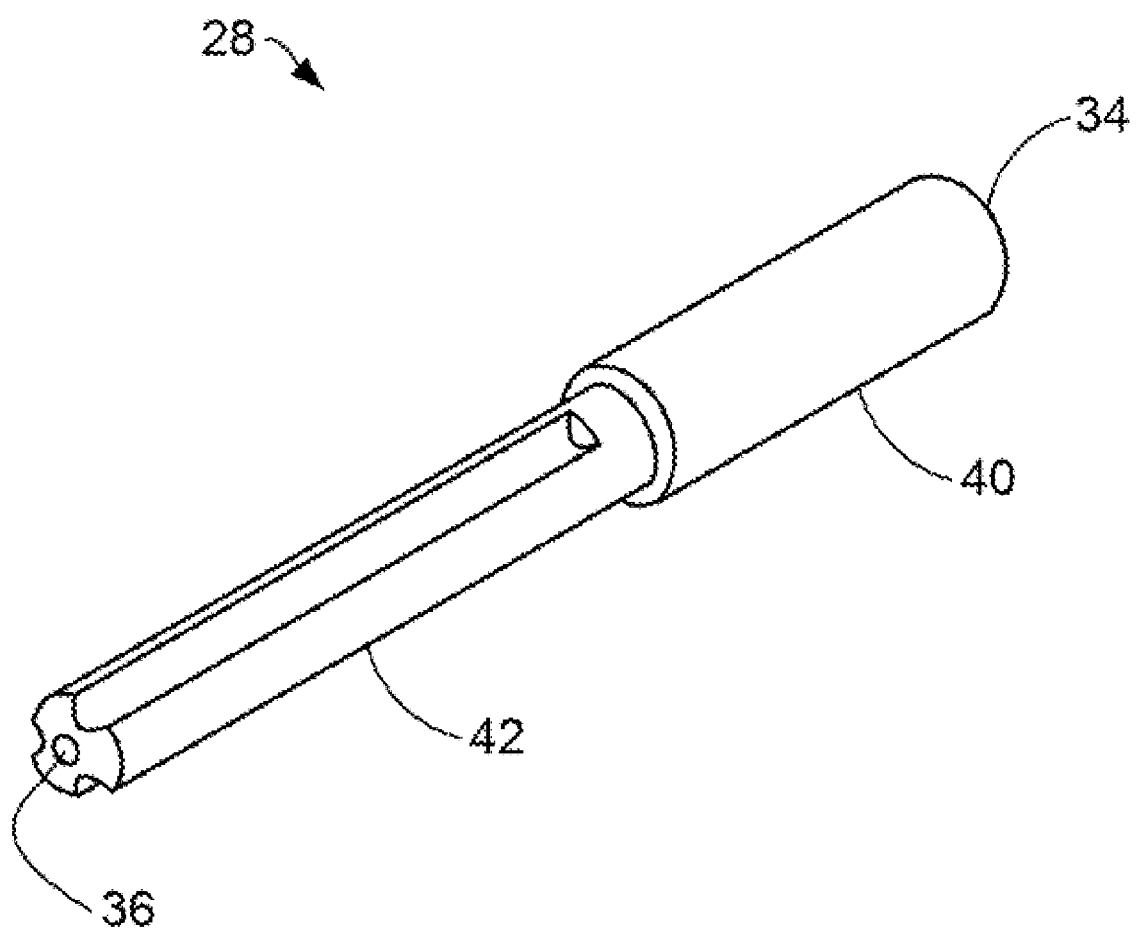
FIGS. 3A-3C illustrate various embodiments of a proximal link of the core mechanism.
Figure 3B:
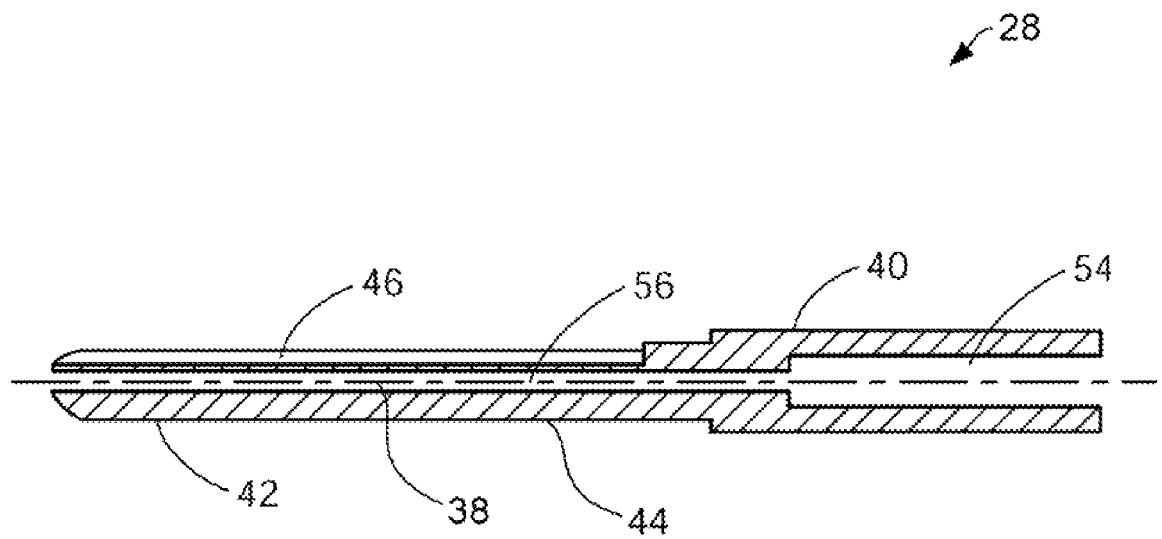
Figure 3C:
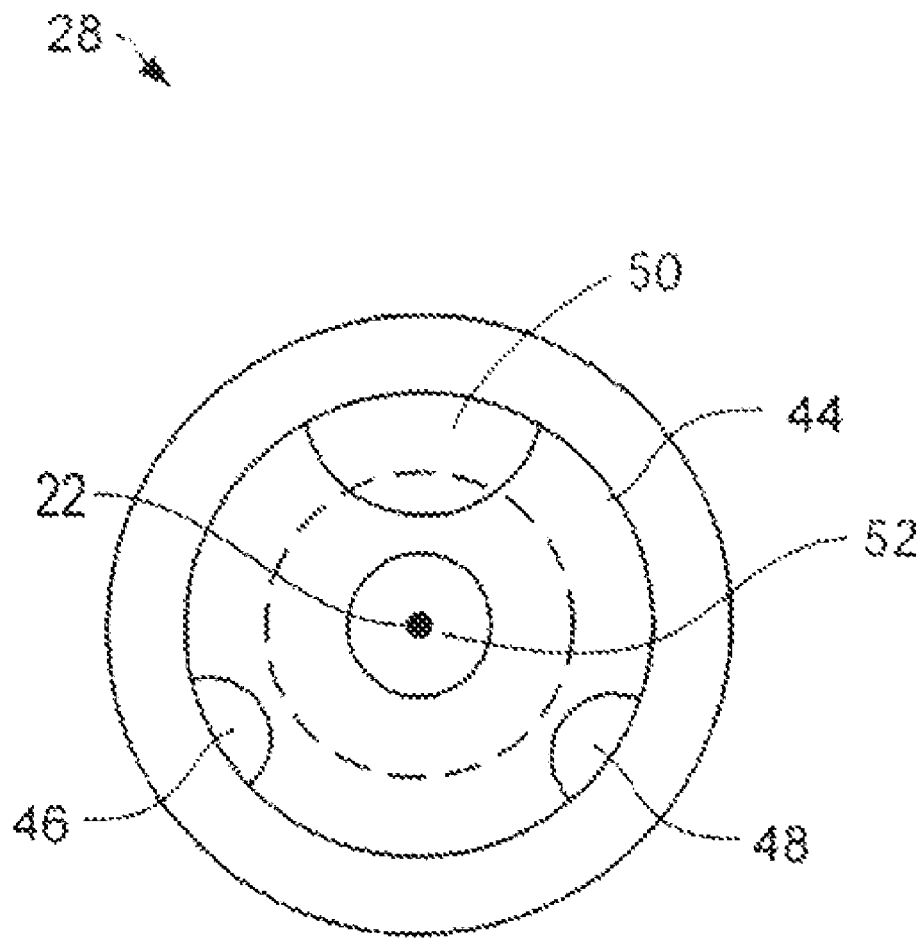

FIGS. 3A-3C illustrate various embodiments of the first link 28 (inner proximal link) of the first mechanism 12. The first link 28 includes a first end 34 and a second end 36, and defines a longitudinal axis 38 that passes through the center of the first end 34 and the center of the second end 36 as shown in FIG. 3B. The first link 28 may be fabricated from any suitable material. According to various embodiments, the first link 28 is fabricated from a fiber reinforced material such as, for example, G10/FR4 Garolite®. The first link 28 has a generally cylindrical shaped exterior and is described in more detail hereinbelow.

The first link 28 includes a first portion 40 and a second portion 42. The first portion 40 may be considered the proximal portion and the second portion 42 may be considered the distal portion. The first portion 40 may be fabricated integral with the second portion 42. The first portion 40 has a cylindrical shaped exterior, and extends from the first end 34 of the first link 28 toward the second end 36 of the first link 28. According to various embodiments, the diameter of the first portion 40 is on the order of approximately 6.35 millimeters.

The second portion 42 has a generally cylindrically shaped exterior. The second portion 42 has a cylindrically shaped exterior where it contacts the first portion 40, and tapers toward the second end 36 of the first link 28. The second portion 42 may be shaped in the form of a generally segmented hemisphere at the second end 36 of the first link 28. According to various embodiments, the diameter of the second portion 42 is on the order of approximately 4.75 millimeters where it contacts the first portion 40.

The second portion 42 includes a first surface 44. The first surface 44 may be considered the outer surface of the second portion 42. The second portion 42 defines a first groove 46 parallel to the longitudinal axis 38 along the first surface 44, a second groove 48 parallel to the longitudinal axis 38 along the first surface 44, and a third groove 50 parallel to the longitudinal axis 38 along the first surface 44. Each of the first, second and third grooves 46, 48, 50 extend along the first surface 44 toward the second end 36 of the first link 28. The first, second and third grooves 46, 48, 50 may be semi-tubular shaped and may be evenly spaced about the first surface 44 of the second portion 42 of the first link 28 as shown in FIG. 3C. According to various embodiments, the first, second, and third grooves 46, 48, 50 may be configured in the shape of a segmented cylinder. The size of each of the grooves 46, 48, 50 may identical to one another or may be different from one another. For example, according to various embodiments, the first and second grooves 46, 48 are configured as segments of a cylinder having a diameter on the order of approximately 1.25 millimeters, and the third groove 50 is configured as a segment of a cylinder having a diameter on the order of approximately 2.50 millimeters. The length of the first link 28 may be on the order of approximately 65 millimeters. However, one skilled in the art will appreciate that the length of the first link 28 can van based on the application.

The first link 28 also defines a passage 52 extending from the first end 34 to the second end 36 along the longitudinal axis 38 as shown in FIG. 3B. The passage 52 is of a size sufficient to allow tile fourth cable 22 to pass therethrough. According to various embodiments, the passage 52 is generally configured as a complex shape that includes a combination of a first cylinder 54 that extends from the first end 34 toward the second end 36, and a second cylinder 56 that extends from the first cylinder 54 toward the second end 36. The diameter of the first cylinder 54 is larger than the diameter of the second cylinder 56. For example, according to various embodiments, the first cylinder 54 has a diameter on the order of approximately 3.20 millimeters and the second cylinder 56 has a diameter on the order of approximately 1.50 millimeters.

Figure 4A:
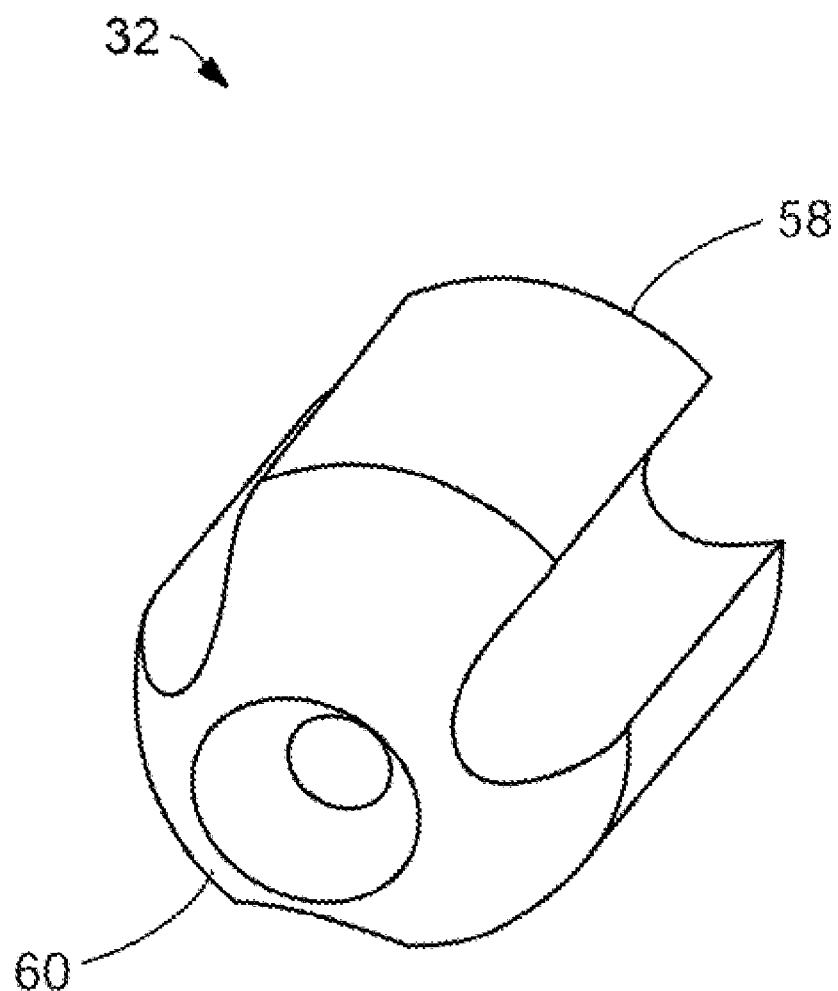
FIGS. 4A-4C illustrate various embodiments of an intermediate link of the core mechanism.
Figure 4B:
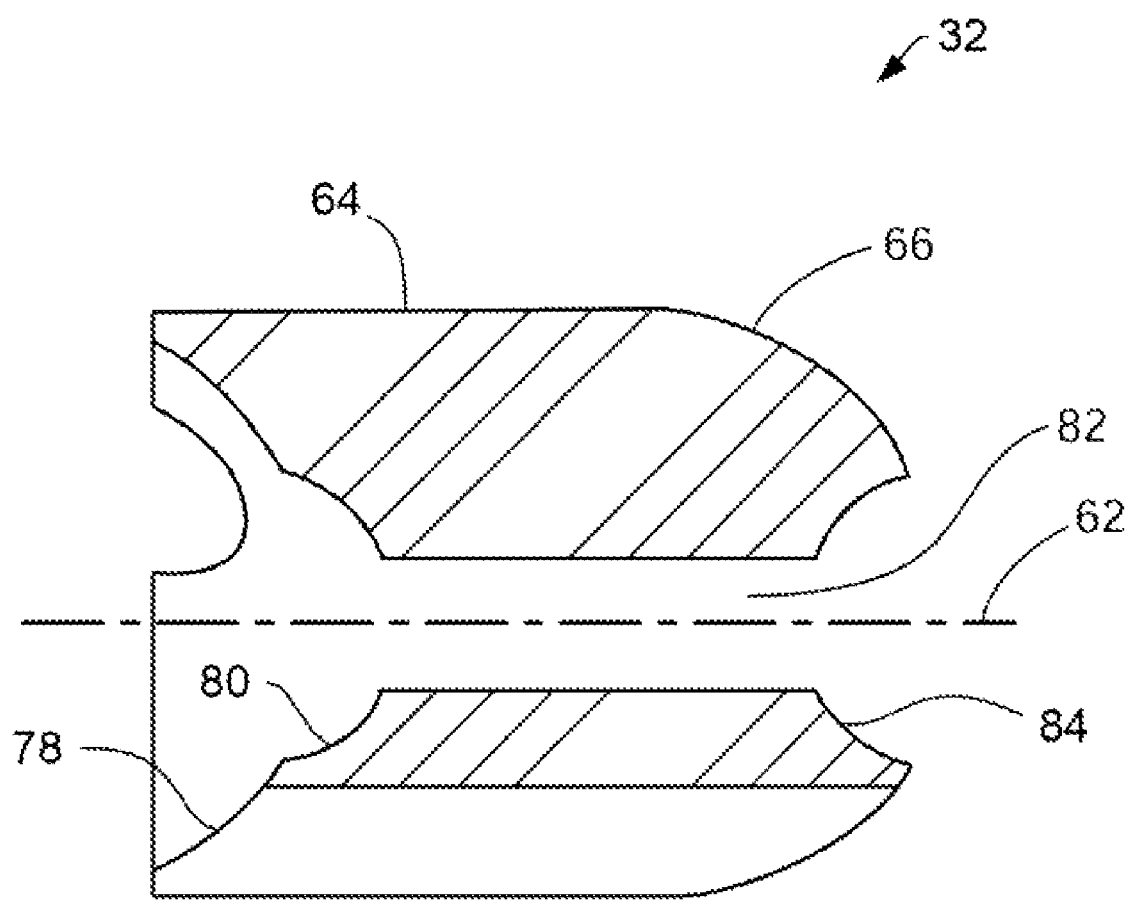
Figure 4C:
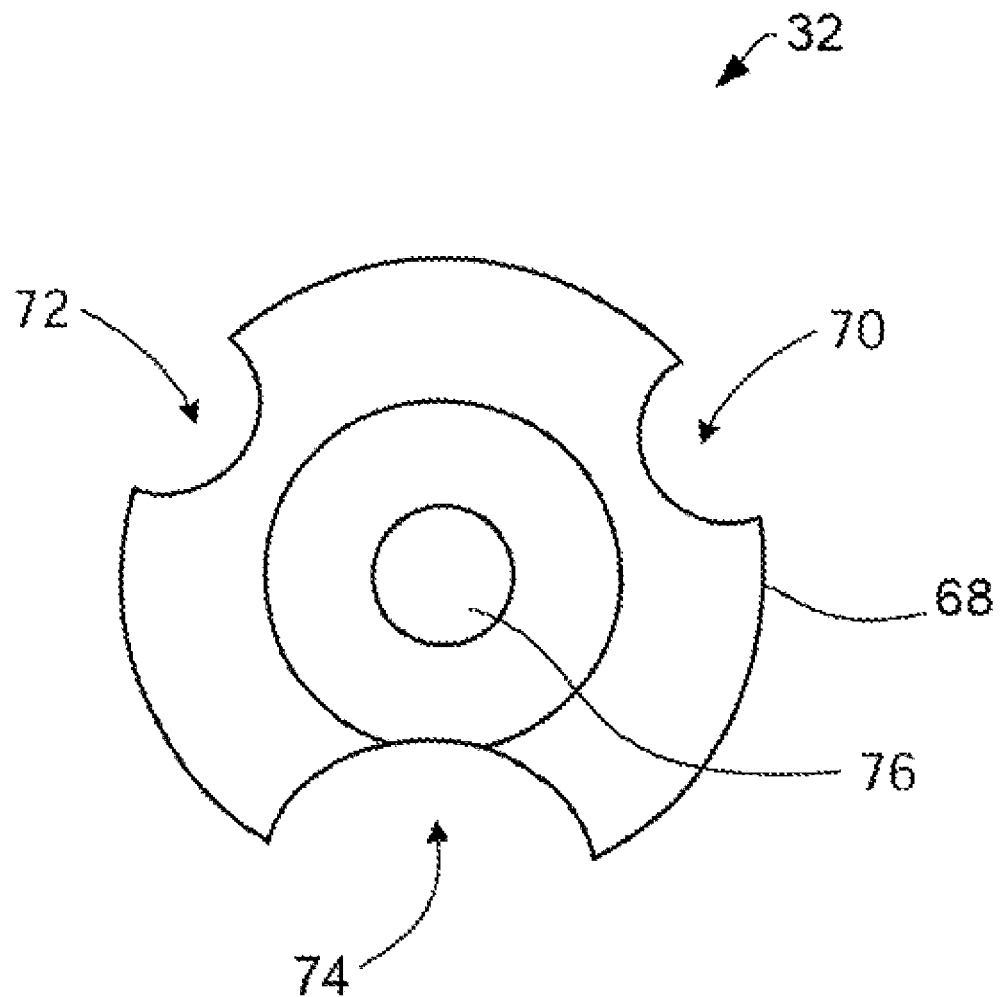

FIGS. 4A-4C illustrate various embodiments of one of the intermediate links 32 (inner intermediate link) of the first mechanism 12. The intermediate link 32 is representative of the other intermediate links 32. The intermediate link 32 includes a first end 58 and a second end 60, and defines a longitudinal axis 62 that passes through the center of the first end 58 and the center of the second end 60 as shown in FIG. 4B. The intermediate link 32 may be fabricated from any suitable material. According to various embodiments, the intermediate link 32 is fabricated from a fiber reinforced material such as, for example, G10/FR4 Garolite®. The intermediate link 32 has a generally bullet-shaped exterior and is described in more detail hereinbelow.

The intermediate link 32 includes a first portion 64 and a second portion 66. The first portion 64 may be considered the proximal portion and the second portion 66 may be considered the distal portion. The first portion 64 may be fabricated integral with the second portion 66. The first portion 64 has a generally cylindrical shaped exterior, and extends from the first end 58 of the intermediate link 32 toward the second end 60 of the intermediate link 32. According to various embodiments, the second portion 66 has a generally cylindrically shaped exterior where it contacts the first portion 64 and tapers toward the second end 60 of the intermediate link 32. The exterior of the second portion 66 is configured in the form of a generally segmented hemisphere. According to various embodiments, the diameter of the intermediate link 32 is on the order of approximately 4.75 millimeters at the first end 58 thereof. The length of the intermediate link 32 may be on the order of approximately 5.85 millimeters. However, one skilled in the art will appreciate that the length of the intermediate link 32 can vary based on the application.

The intermediate link 32 also includes a first surface 68 that extends from the first end 58 of the intermediate link 32 to the second end 60 of the intermediate link 32. The first surface 68 may be considered the outer surface of the intermediate link 32. The intermediate link 32 also defines a first groove 70 parallel to the longitudinal axis 62 along the first surface 68, a second groove 72 parallel to the longitudinal axis 62 along the first surface 68, and a third groove 74 parallel to the longitudinal axis 62 along the first surface 68. Each of the first, second and third grooves 70, 72, 74 extend along the first surface 68 from the first end 58 of the intermediate link 32 toward the second end 60 of the intermediate link 32. The first, second and third grooves 70, 72, 74 may be semi-tubular shaped and may be evenly spaced about the first surface 68 of the intermediate link 32 as shown in FIG. 4C. According to various embodiments the first, second, and third grooves 70, 72, 74 may be configured in the shape of a segmented cylinder. The size of each of the grooves 70, 72, 74 may identical to one another or may be different from one another. For example, according to various embodiments, the first and second grooves 70, 72 are configured as segments of a cylinder having a diameter on the order of approximately 1.75 millimeters at the first end 58 of the intermediate link 32, and the third groove 74 is configured as a segment of a cylinder having a diameter on the order of approximately 2.50 millimeters at the first end 58 of the intermediate link 32. The first, second and third grooves 70, 72, 74 are each configured to receive and partially surround any of a variety of tools or instruments (e.g., ablation tools) which may pass from the first end 24 of the multi-linked device 1I to the second end 26 of the multi-linked device 10.

The intermediate link 32 also defines a passage 76 extending from the first end 58 to the second end 60 along the longitudinal axis 62 as shown in FIG. 4B. The passage 76 is of a size sufficient to allow the fourth cable 22 to pass therethrough. According to various embodiments, the passage 76 is generally configured as a complex shape that includes a combination of a first segmented hemisphere 78 that extends from the first end 58 toward the second end 60, a second segmented hemisphere 80 that extends from the first segmented hemisphere 78 toward the second end 60, a cylinder 82 that extends from the second segmented hemisphere 80 toward the second end 60, and a third segmented hemisphere 84 that extends from the cylinder 82 to the second end 60 of the intermediate link 32. According to various embodiments, the first segmented hemisphere 78 represents a portion of a sphere having a diameter on the order of approximately 4.75 millimeters, the second segmented hemisphere 80 represents a portion of a sphere having a diameter on the order of approximately 2.25 millimeters, the cylinder 82 has a diameter on the order of approximately 1.0 millimeter, and the third segmented hemisphere 84 represents a portion of a sphere having a diameter on the order of approximately 2.25 millimeters.

The first segmented hemisphere 78 of the passage 76 is configured to receive the second end 36 of the first link 28 when the first link 28 is coupled to the intermediate link 32. Similarly, for a given intermediate link 32, the first segmented hemisphere 78 of the passage 76 is configured to receive the second end 60 of another intermediate link 32 when the other intermediate link 32 is coupled to the given intermediate link 32. The third segmented hemisphere 84 may serve to reduce the pinching or binding of the fourth cable 22 when one intermediate link 32 moves relative to an adjacent intermediate link 32 coupled thereto. Similarly, when the second link 30 is coupled to a given intermediate link 32, the third segmented hemisphere 84 may serve to reduce the pinching or binding of the fourth cable 22 when the second link 30 moves relative to the given intermediate link 32.

With the above described structure, the first link 28 may be coupled to the intermediate link 32 by seating the second end 36 of the first link 28 in the first segmented hemisphere 78 of the passage 76 of the intermediate link 32. As the convex configuration of the second end 36 of the first link 28 generally corresponds with the concave configuration of the first segmented hemisphere 78 of the passage 76 of the intermediate link 32, the first link 28 may be coupled to the intermediate link 32 such that the longitudinal axis 38 and the first, second and third grooves 46, 48, 50 of the first link 28 are respectively aligned with the longitudinal axis 62 and the first, second and third grooves 70, 72, 74 of the intermediate link 32. The intermediate link 32 may be moved relative to the first link 28 such that the longitudinal axis 62 of the intermediate link 32 is not aligned with the longitudinal axis 38 of the first link 28. According to various embodiments, the configuration of the first link 28 and the intermediate link 32 allows for the intermediate link 32 to be moved relative to the first link 28 coupled thereto such that the longitudinal axis 38 of the first link 28 and the longitudinal axis 62 of the intermediate link 32 are up to approximately 25° out of alignment with one another. Similarly, one intermediate link 32 may be coupled to another intermediate link 32, and so on, by seating the second end 60 of one intermediate link 32 in the first segmented hemisphere 78 of the passage 76 of another intermediate link 32. As the convex configuration of the second end 60 of the intermediate link 32 generally corresponds with the concave configuration of the first segmented hemisphere 78 of the passage 76 of the intermediate link 32, the intermediate links 32 may be coupled such that the respective longitudinal axes 62 and the respective first, second and third grooves 46, 48, 50 of the intermediate links 32 are aligned. The coupled intermediate links 32 may be moved relative to one another such that the respective longitudinal axes 62 of the coupled intermediate links 32 are not aligned. According to various embodiments, the configuration of the coupled intermediate links 32 allows for one intermediate link 32 to be moved relative to an adjacent intermediate link 32 coupled thereto such that the respective longitudinal axes 62 are up to approximately 25° out of alignment with one another.

Figure 5A:
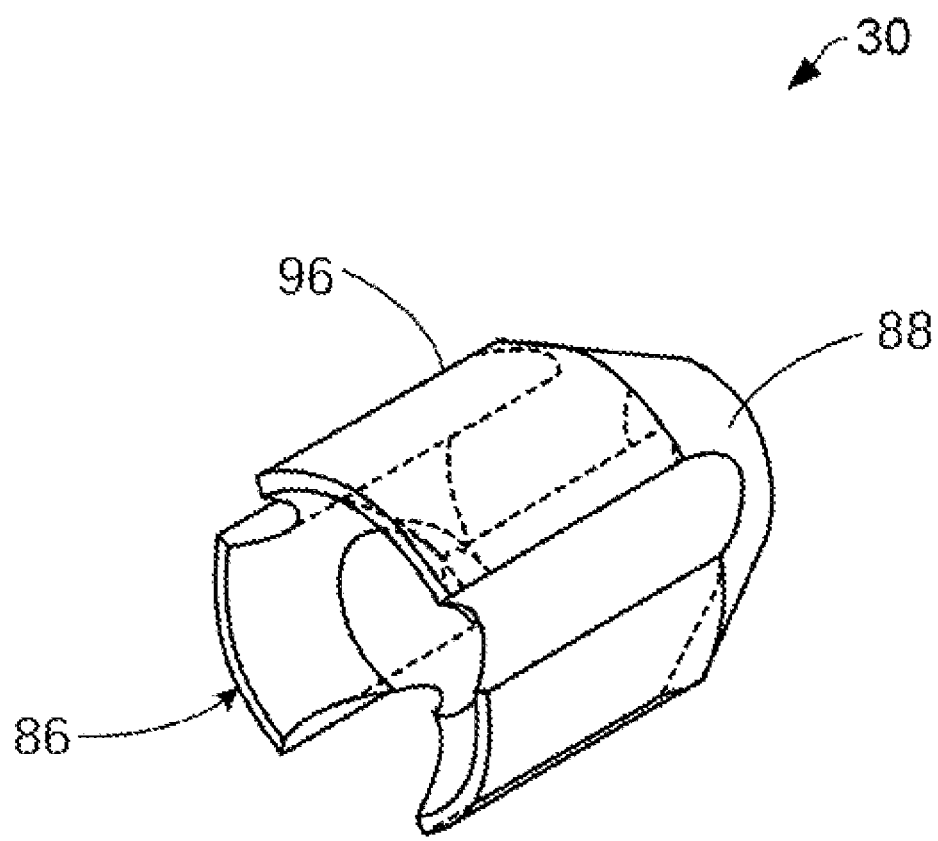
FIGS. 5A-5C illustrate various embodiments of a distal link of the core mechanism.
Figure 5B:
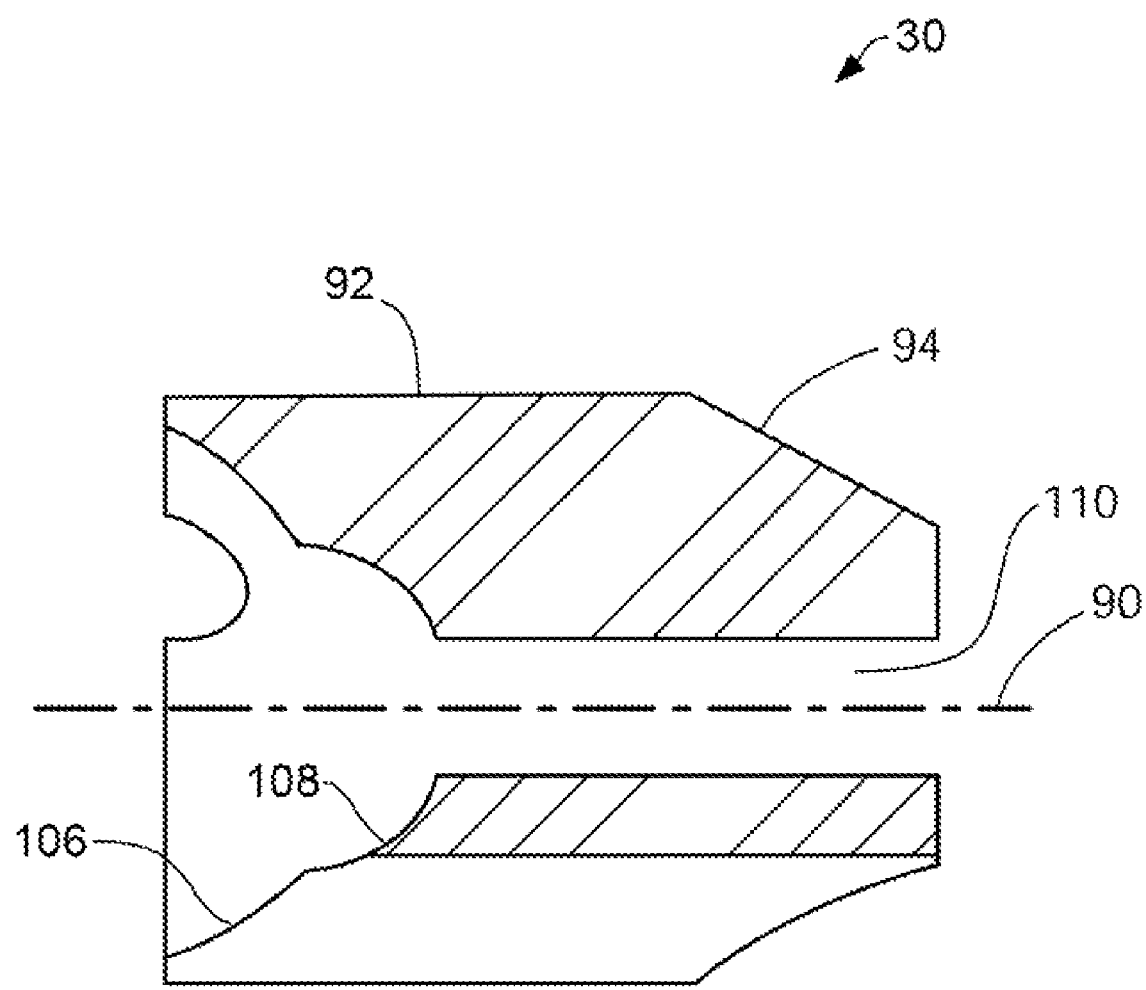
Figure 5C:
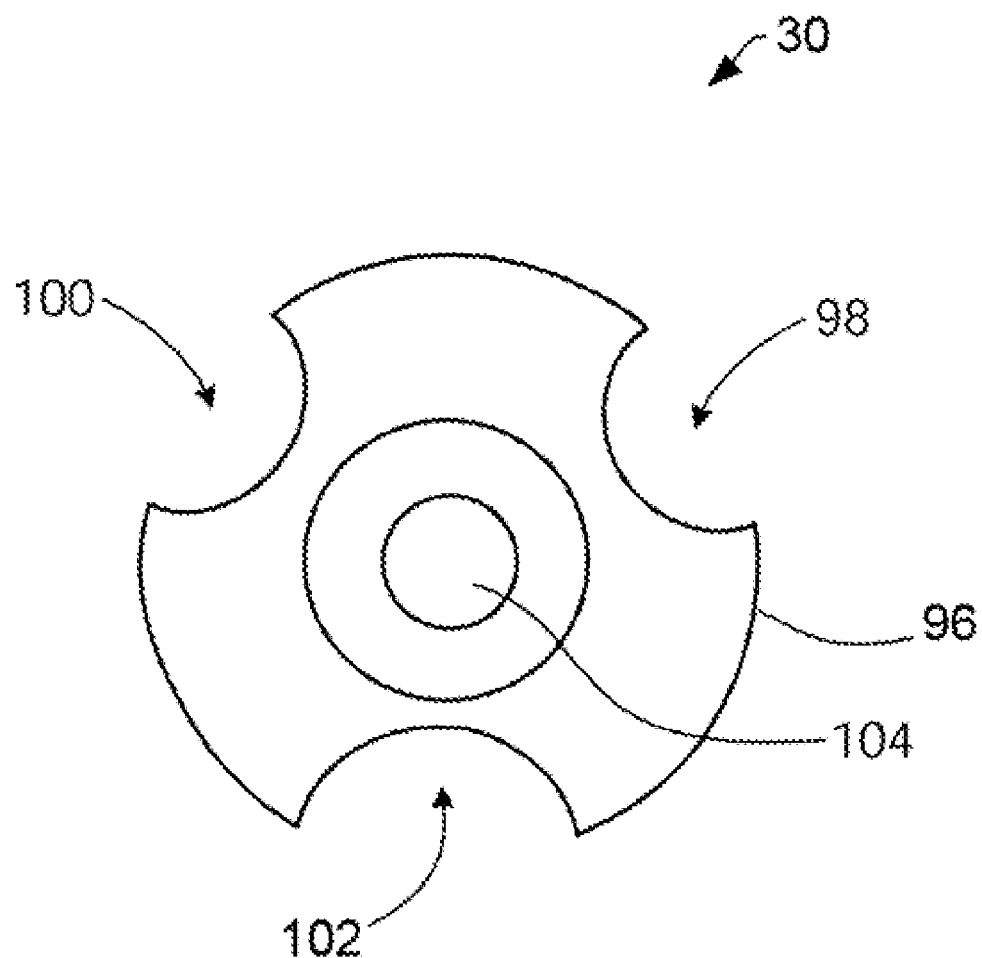

FIGS. 5A-5C illustrate various embodiments of the second link 30 (inner distal link) of the first mechanism 12. The second link 30 includes a first end 86 and a second end 38, and defines a longitudinal axis 90 that passes through the center of the first end 86 and the center of the second end 88 as shown in FIG. 5B. The second link 30 may be fabricated from any suitable material. According to various embodiments, the second link 30 is fabricated from a thermoplastic material such as, for example, Delrin®.

The second link 30 includes a first portion 92 and a second portion 94. The first portion 92 may be considered the proximal portion and the second portion 94 may be considered the distal portion. The first portion 92 may be fabricated integral with the second portion 94. The first portion 92 has a generally cylindrical shaped exterior, and extends from the first end 86 of the second link 30 toward the second end 88 of the second link 30. According to various embodiments, the second portion 94 has a generally cylindrically shaped exterior where it contacts the first portion 92, and tapers toward the second end 88 of the second link 30. The exterior of the second portion 64 is configured in the form of a generally segmented cone. According to various embodiments, the diameter of the second link 30 is on the order of approximately 4.75 millimeters at the first end 86 thereof, and the taper of the second portion 94 is at an angle of approximately 30° relative to the exterior of the first portion 92. The length of the second link 30 may be on the order of approximately 5.90 millimeters. However, one skilled in the art will appreciate that the length of the second link 30 can vary based on the application.

The second link 30 also includes a first surface 96 that extends from the first end 86 of the second link 30 to the second end 88 of the second link 30. The first surface 96 may be considered the outer surface of the second link 30. The second link 30 also defines a first groove 98 parallel to the longitudinal axis 90 along the first surface 96, a second groove 100 parallel to the longitudinal axis 90 along the first surface 96, and a third groove 102 parallel to the longitudinal axis 90 along the first surface 96. Each of the first, second and third grooves 98, 100, 102 extend along the first surface 96 from the first end 86 of the second link 30 toward the second end 88 of the second link 30. The first, second and third grooves 98, 100, 102 may be semi-tubular shaped and may be evenly spaced about the first surface 96 of the second link 30 as shown in FIG. 5C. According to various embodiments, the first, second, and third grooves 98, 100, 102 may be configured in the shape of a segmented cylinder. The size of each of the grooves 98, 100, 102 may identical to one another or may be different from one another. For example, according to various embodiments, the first and second grooves 98, 100 are configured as segments of a cylinder having a diameter on the order of approximately 125 millimeters at the first end 86 of the second link 30, and the third groove 102 is configured as a segment of a cylinder having a diameter on the order of approximately 2.50 millimeters at the first end 86 of the second link 30. The first, second and third grooves 98, 100, 102 are each configured to receive and partially surround any of a variety of tools or instruments (e.g., ablation tools) which may pass from the first end 24 of the multi-linked device 10 to the second end 26 of the multi-linked device 10.

The second link 30 also defines a passage 104 extending from the first end 86 to the second end 88 along the longitudinal axis 90 as shown in FIG. 5B. The passage 104 is of a size sufficient to allow the fourth cable 22 to pass therethrough. According to various embodiments, the passage 104 is generally configured as a complex shape that includes a combination of a first segmented hemisphere 106 that extends from the first end 86 toward the second end 88, a second segmented hemisphere 108 that extends from the first segmented hemisphere 106 toward the second end 88, and a cylinder 110 that extends from the second segmented hemisphere 108 to the second end 88 of the second link 30. According to various embodiments, the first segmented hemisphere 106 represents a portion of a sphere having a diameter on the order of approximately 4.75 millimeters, the second segmented hemisphere 108 represents a portion of a sphere having a diameter on the order of approximately 2.50 millimeters, and the cylinder 110 has a diameter on the order of approximately 1.0 millimeter. The first segmented hemisphere 106 of the passage 104 is configured to receive the second end 60 of an intermediate link 32 when the intermediate link 32 is coupled to the second link 30.

With the above described structure, an intermediate link 32 may he coupled to the second link 30 by seating the second end 60 of the intermediate link 32 in the first segmented hemisphere 106 of the passage 104 of the second link 30. As the convex configuration of the second end 60 of the intermediate link 32 generally corresponds with the concave configuration of the first segmented hemisphere 106 of the passage 104 of the second link 30, the intermediate link 32 may be coupled to the second link 30 such that the longitudinal axis 62 and the first, second and third grooves 70, 72, 74 of the intermediate link 32 are respectively aligned with the longitudinal axis 90 and the first, second and third grooves 98, 100, 102 of the second link 30. The second link 30 may be moved relative to the intermediate link 32 coupled thereto such that the respective longitudinal axes 62, 90 are not aligned. According to various embodiments, the configuration of the second link 30 allows for an intermediate link 32 coupled thereto to be moved relative to the second link 30 such that the respective longitudinal axes 62, 90 are up to approximately 25° out of alignment with one another.

Figure 6:
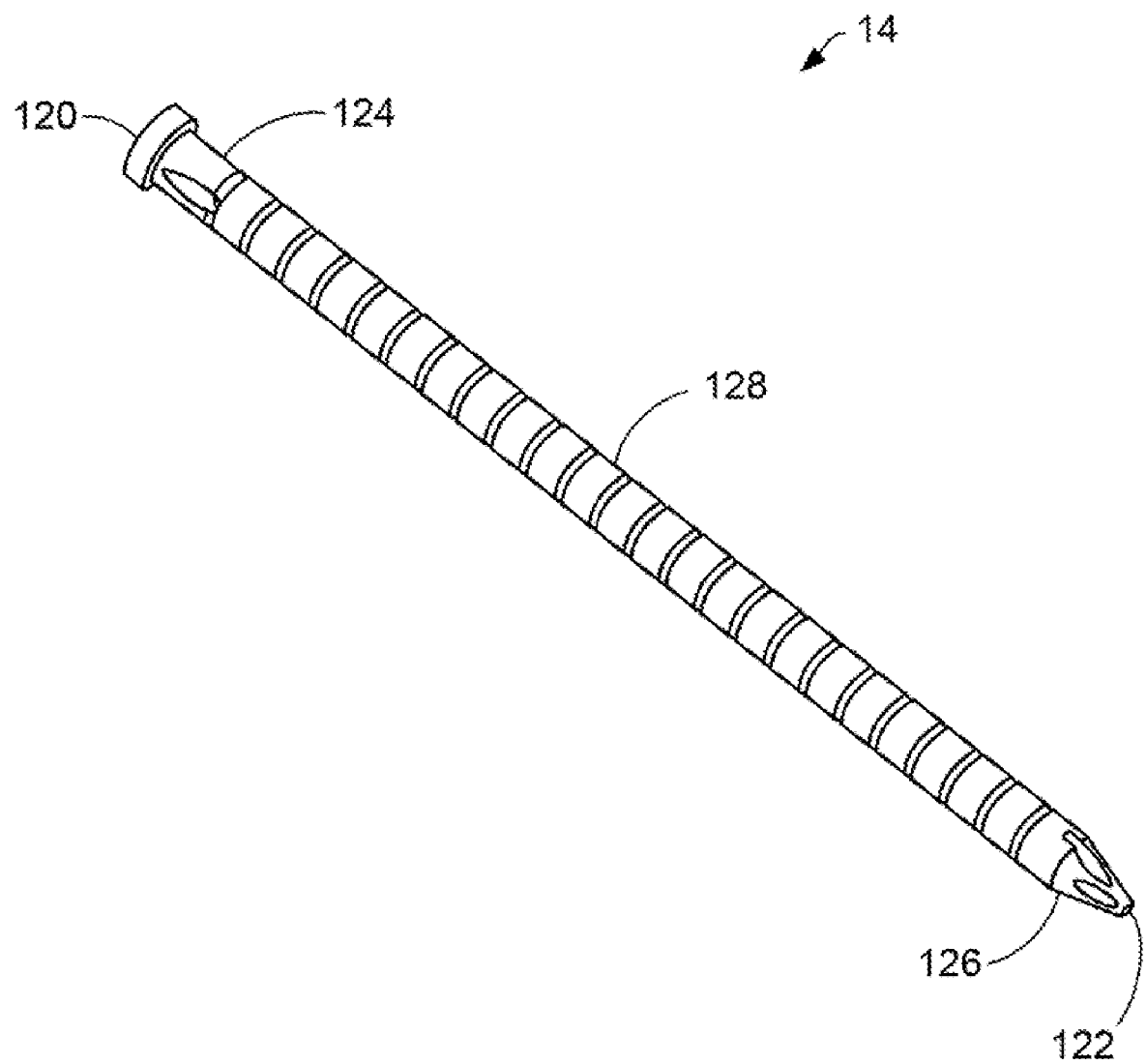
FIG. 6 illustrates various embodiments of a sleeve mechanism of the device of FIG. 1.

FIG. 6 illustrates various embodiments of the second mechanism 14 of the device 10. The second mechanism 14 is a multi-linked mechanism and includes a first end 120 and a second end 122. The first end 120 may be considered the proximal end and the second end 122 may be considered the distal end. The second mechanism 14 includes a first link 124, a second link 126, and any number of intermediate links 128 between the first and second links 124, 126. The first link 124 may be considered the proximal link, and the second link 126 may be considered the distal link.

Figure 7A:
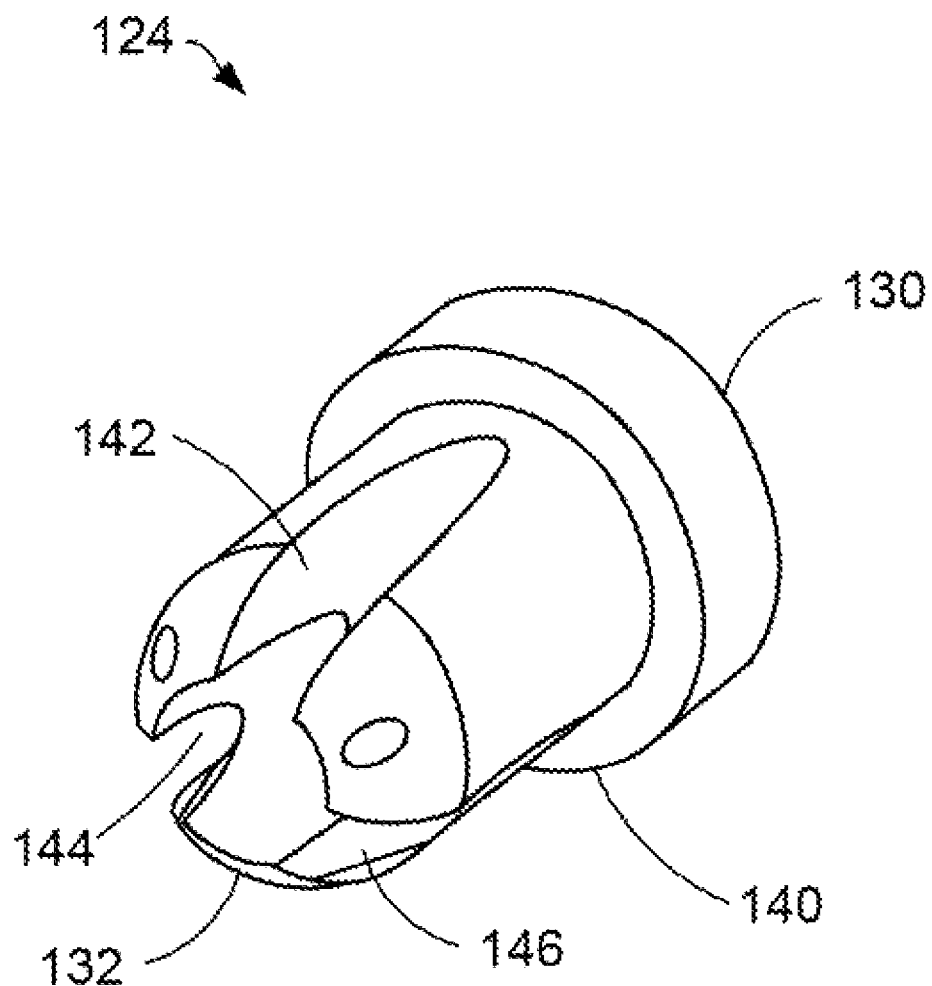
FIGS. 7A-7C illustrate various embodiments of a proximal link of the sleeve mechanism 1.
Figure 7B:
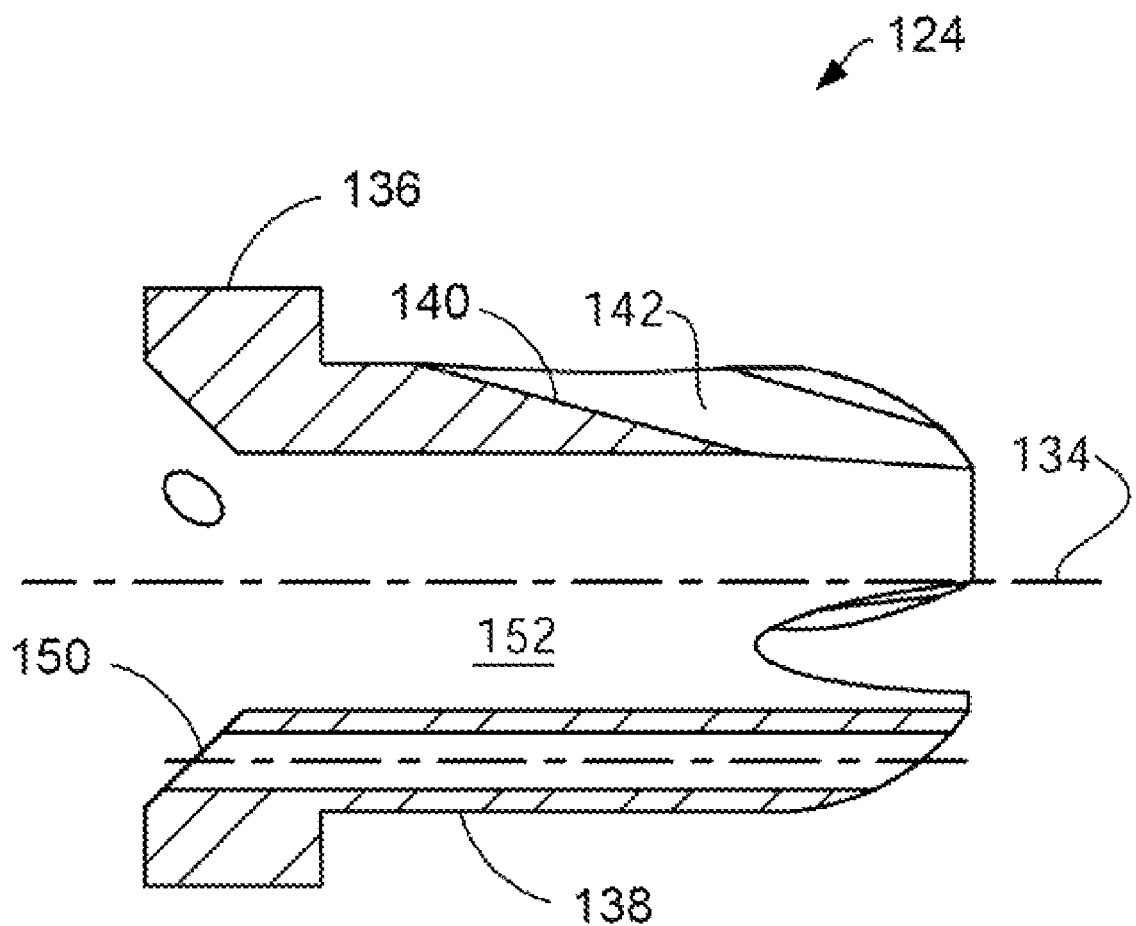
Figure 7C:
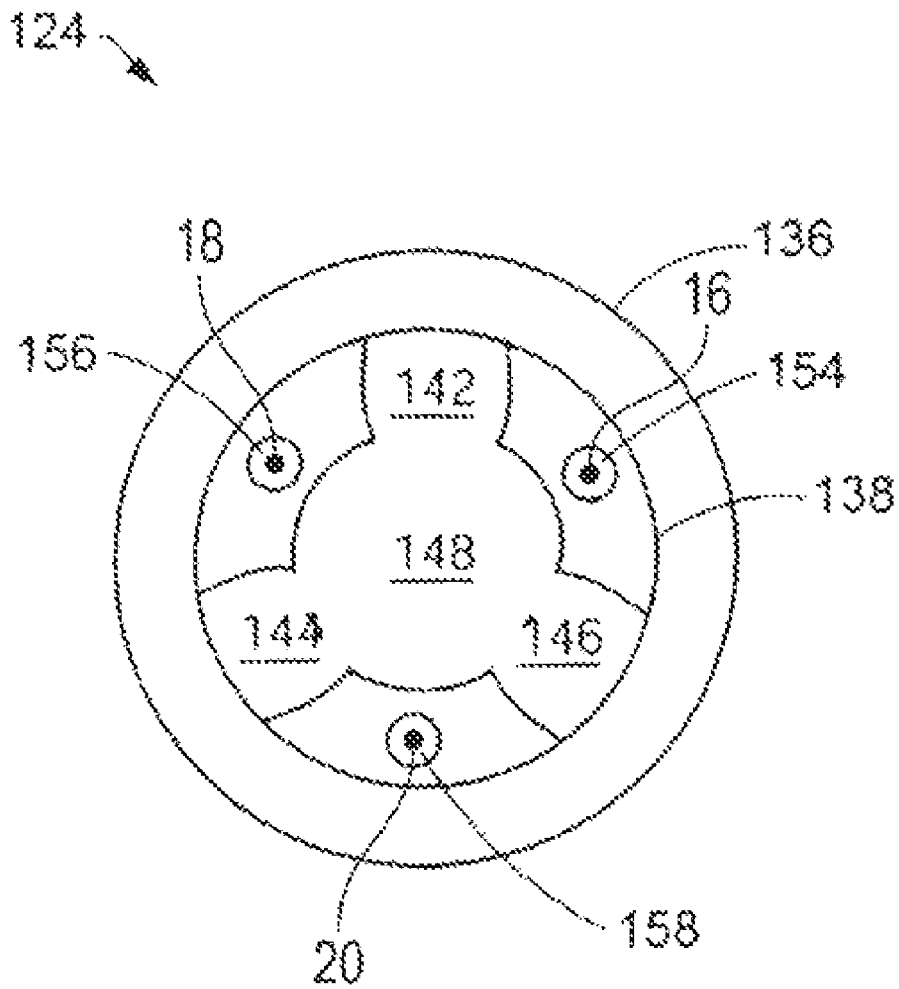

FIGS. 7A-7C illustrate various embodiments of the first link 124 (outer proximal link) of the second mechanism 14. The first link 124 includes a first end 130 and a second end 132, and defines a longitudinal axis 134 that passes through the center of the first end 130 and the center of the second end 132 as shown in FIG. 7B. The first link 124 may be fabricated from any suitable material. According to various embodiments, the first link 124 is fabricated from a stainless steel material such as, for example, 316 stainless steel. The first link 124 has a generally bullet-shaped exterior and is described in more detail hereinbelow.

The first link 124 includes a first portion 136 and a second portion 138. The first portion 136 may be considered the proximal portion and the second portion 138 may be considered the distal portion. The first portion 136 may be fabricated integral with the second portion 138. The first portion 136 has a cylindrical shaped exterior, and extends from the first end 130 of the first link 124 toward the second end 132 of the first link 124. According to various embodiments, the diameter of the first portion 136 is on the order of approximately 12.70 millimeters.

The second portion 138 has a generally cylindrically shaped exterior. The second portion 138 has a cylindrically shaped exterior where it contacts the first portion 136, and tapers toward the second end 132 of the first link 124. The second portion 138 may be shaped in the form of a generally segmented hemisphere at the second end 132 of the first link 124. According to various embodiments, the diameter of the second portion 138 is on the order of approximately 9.50 millimeters where it contacts the first portion 136.

The second portion 138 includes a first surface 140. The first surface 140 may be considered the outer surface of the second portion 138. The second portion 138 defines a first groove 142 along the first surface 140, a second groove 144 along the first surface 140, and a third groove 146 along the first surface 140. Each of the first, second and third grooves 142, 144, 146 are oblique relative to the longitudinal axis 134 and extend along the first surface 140 toward the second end 132 of the first link 124. According to various embodiments, each of the grooves 142, 144, 146 are oriented at an angle on the order of approximately 15° relative to the longitudinal axis 134. As shown in FIG. 7C, the first, second and third grooves 142, 144, 146 may be evenly spaced about the first surface 140 of the first link 124. According to various embodiments, the first, second, and third grooves 142, 144, 146 may be configured in the shape of a segmented cylinder. The size of each of the grooves 142, 144, 146 may identical to one another or may be different from one another. For example, according to various embodiments, each of the grooves 142, 144, 146 are configured as segments of respective cylinders having diameters on the order of approximately 3.0 millimeters. The first, second and third grooves 142, 144, 146 are each configured to facilitate the introduction various tools or instruments (e.g., ablation tools) into the multi-linked device 10. The length of the first link 124 may be on the order of approximately 18.5 millimeters. However, one skilled in the art will appreciate that the length of the first link 124 can vary based on the application.

The first link 124 also defines a passage 148 extending from the first end 130 to the second end 132 along the longitudinal axis 134 as shown in FIG. 7B. The passage 148 is of a size sufficient to allow the first mechanism 12 to pass therethrough. According to various embodiments, the passage 148 is generally configured as a complex shape that includes a combination of a segmented cone 150 that extends from the first end 130 toward the second end 132, and a cylinder 152 that extends from the segmented cone 150 to the second end 132 of the first link 124. According to various embodiments, the segmented cone 150 has a diameter on the order of approximately 7.0 millimeters at the first end 130 of the first link 124, and is tapered at an angle on the order of approximately 45° relative to the longitudinal axis 134. The cylinder 152 has a diameter on the order of approximately 5.50 millimeters.

The first link 124 also defines a first through-hole 154, a second through-hole 156, and a third through-hole 158. (See FIG. 7C). The first through-hole 154 is substantially parallel to the longitudinal axis 134, extends from the first portion 136 toward the second end 132, and is positioned between the passage 148 and the first surface 140. The second through-hole 156 is substantially parallel to the longitudinal axis 134, extends from the first portion 136 to the second end 132, and is positioned between the passage 148 and the first surface 140. The third through-hole 158 is substantially parallel to the longitudinal axis 134, extends from the first portion 136 to the second end 132, and is positioned between the passage 148 and the first surface 140. The first, second and third through-holes 154, 156, 158 are generally cylindrically shaped. According to various embodiments, the through-holes 154, 156, 158 are evenly spaced from one another as shown in FIG. 7C. The size of each of the through-holes 154, 156, 158 may be identical to one another or may be different from one another. For example, according to various embodiments, the respective diameters associated with the through-holes 154, 156, 158 may each be on the order of approximately 1.20 millimeters. The first through-hole 154 is configured to receive and surround the first cable 16. The second through-hole 156 is configured to receive and surround the second cable 18. The third through-hole 158 is configured to receive and surround the third cable 20. The first, second and third through-holes 154, 156, 158 may serve as guidepaths for movement of the first, second and third cables 16, 18, 20.

Figure 8A:
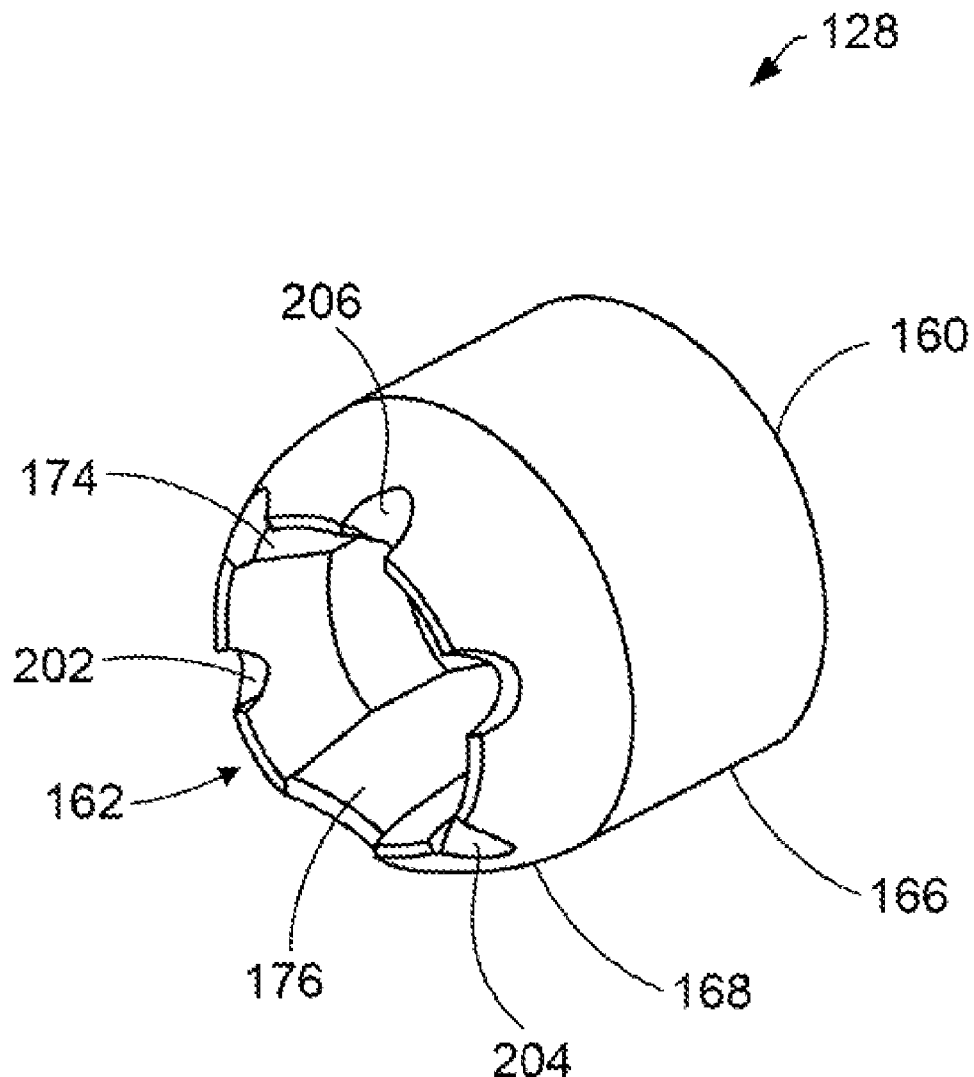
FIGS. 8A-8C illustrate various embodiments of an intermediate link of the sleeve mechanism.
Figure 8B:
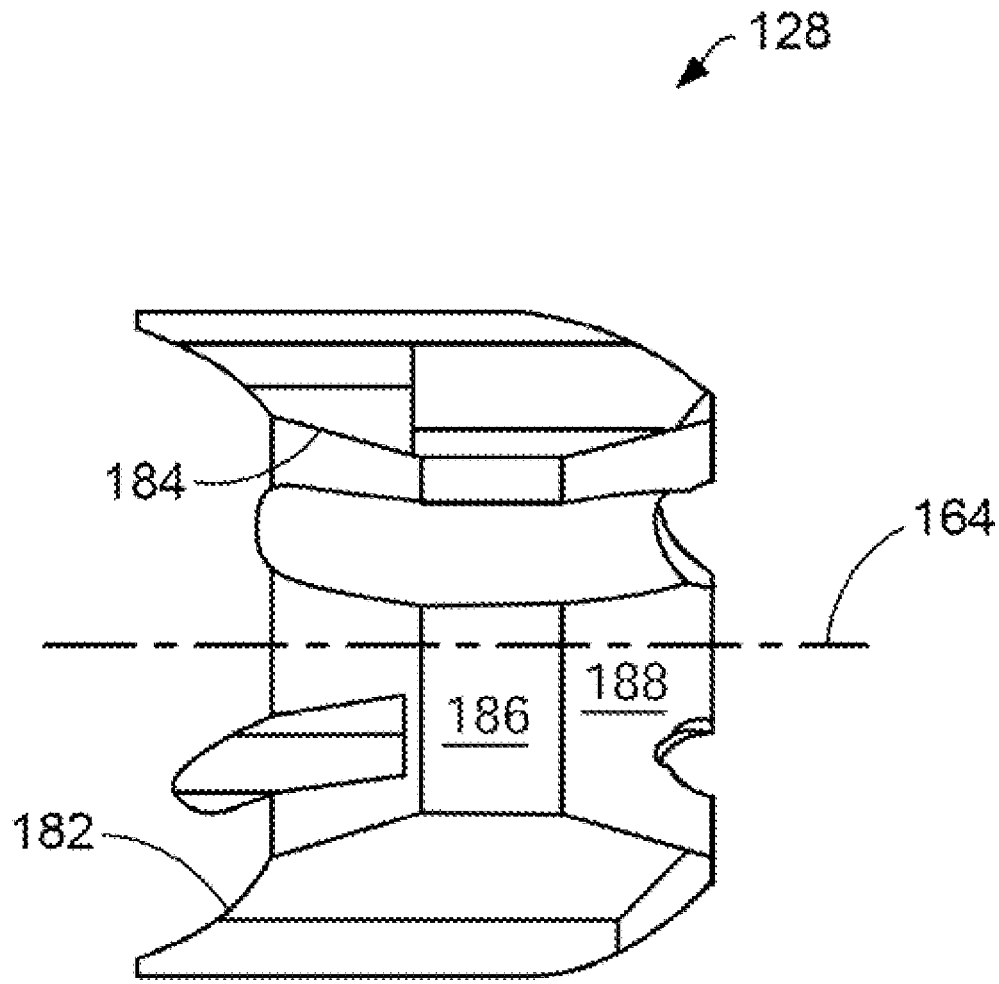
Figure 8C:
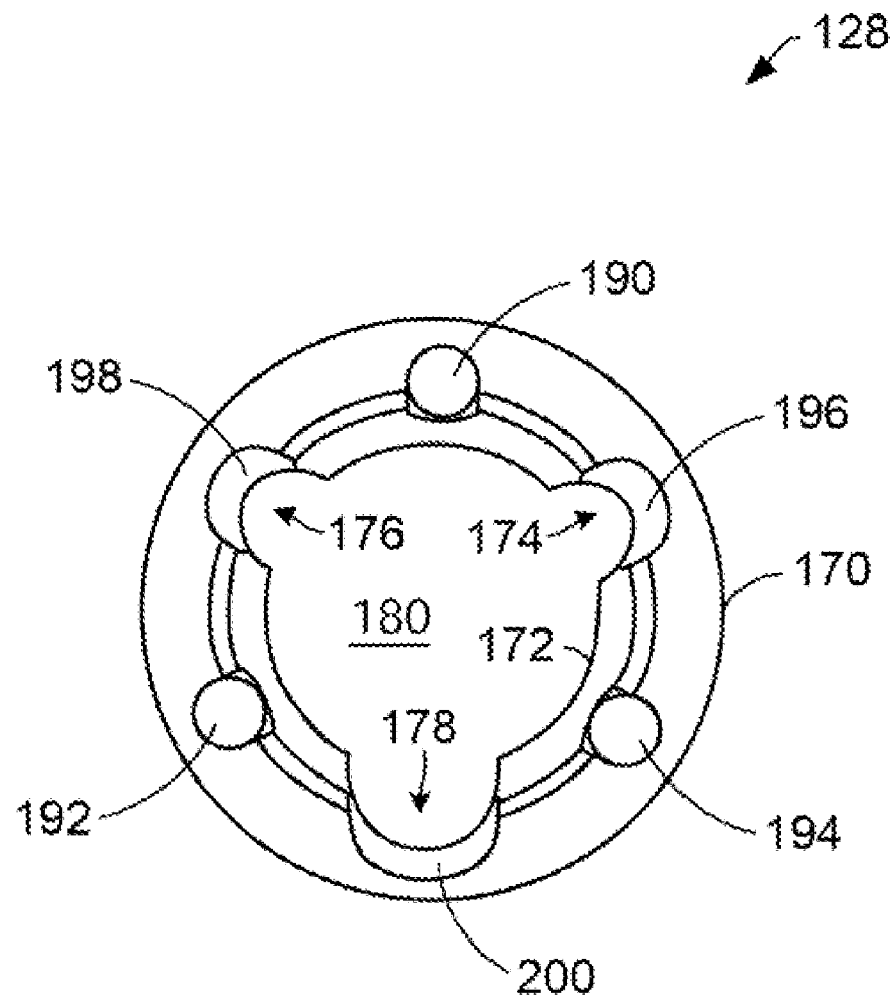

FIGS. 8A-8C illustrate various embodiments of one of the intermediate links 128 (outer intermediate link) of the second mechanism 14. The intermediate link 128 is representative of the other intermediate links 128. The intermediate link 128 includes a first end 160 and a second end 162, and defines a longitudinal axis 164 that passes through the center of the first end 160 and the center of the second end 162 as shown in FIG. 8B. The intermediate link 128 may be fabricated from any suitable material. According to various embodiments, the intermediate link 128 is fabricated from a polymer thermoplastic material such as, for example, polysulfone. The intermediate link 128 has a generally bullet-shaped exterior and is described in more detail hereinbelow.

The intermediate link 128 includes a first portion 166 and a second portion 168. The first portion 166 may be considered the proximal portion and the second portion 168 may be considered the distal portion. The first portion 166 may be fabricated integral with the second portion 168. The first portion 166 has a generally cylindrical shaped exterior, and extends from the first end 160 of the intermediate link 128 toward the second end 162 of the intermediate link 128. According to various embodiments, the second portion 168 has a generally cylindrically shaped exterior where it contacts the first portion 166, and tapers toward the second end 162 of the intermediate link 128. The exterior of the second portion 168 is configured in the form of a generally segmented hemisphere. According to various embodiments, the diameter of the intermediate link 128 is on the order of approximately 9.65 millimeters at the first end 160 thereof. The length of the intermediate link 128 may be on the order of approximately 8.40 millimeters. However, one skilled in the art will appreciate that the length of the intermediate link 128 can vary based on the application.

The intermediate link 128 also includes a first surface 170 that extends from the first end 160 of the intermediate link 128 to the second end 162 of the intermediate link 128, and a second surface 170 that extends from the first end 160 of the intermediate link 128 to the second end 162 of the intermediate link 128. The first surface 170 may be considered the outer surface of the intermediate link 128, and the second surface 172 may be considered the inner surface of the intermediate link 128. The intermediate link 32 also defines a first groove 174 substantially parallel to the longitudinal axis 164 along the second surface 172, a second groove 176 substantially parallel to the longitudinal axis 164 along the second surface 172, and a third groove 178 substantially parallel to the longitudinal axis 164 along the second surface 172. Each of the first, second and third grooves 174, 176, 178 extend along the second surface 172 toward the second end 162 of the intermediate link 128. The first, second and third grooves 174, 176, 178 may be semi-tubular shaped and may be evenly spaced about the second surface 172 of the intermediate link 128 as shown in FIG. 8C. According to various embodiments, the first, second, and third grooves 174, 176, 178 may be configured in the shape of a segmented cylinder. The size of each of the grooves 174, 176, 178 may identical to one another or may be different from one another. For example, according to various embodiments, the first and second grooves 174, 176 are configured as segments of cylinders having diameters on the order of approximately 1.75 millimeters at the first end 160 of the intermediate link 128, and the third groove 178 is configured as a segment of a cylinder having a diameter on the order of approximately 2.50 millimeters at the first end 160 of the intermediate link 128. The first, second and third grooves 174, 176, 178 are each configured to receive and partially surround any of a variety of tools or instruments (e.g., ablation tools) which may pass from the first end 24 of the multi-linked device 10 to the second end 26 of the multi-linked device 10.

The intermediate link 128 also defines a passage 180 extending from the first end 160 to the second end 162 along the longitudinal axis 164 as shown in FIG. 8B. The passage 180 is of a size sufficient to allow the first mechanism 12 to pass therethrough. According to various embodiments, the passage 180 is generally configured as a complex shape that includes a combination of a segmented hemisphere 182 that extends from the first end 160 toward the second end 162, a first segmented cone 184 that extends from the segmented hemisphere 182 toward the second end 162, a cylinder 186 that extends from the first segmented cone 184 toward the second end 162, and a second segmented cone 188 that extends from the cylinder 186 to the second end 162 of the intermediate link 128. According to various embodiments, the segmented hemisphere 182 represents a portion of a sphere having a diameter on the order of approximately 9.65 millimeters, the first segmented cone 184 is tapered at an angle on the order of approximately 15° relative to the longitudinal axis 164, the cylinder 186 has a diameter on the order of approximately 5.50 millimeters, and the second segmented cone 188 is tapered at an angle on the order of approximately 15° relative to the longitudinal axis 164. The segmented hemisphere 182 of the passage 180 is configured to receive the second end 132 of the first link 124 when the first link 124 is coupled to the intermediate link 128. Similarly, for a given intermediate link 128, the segmented hemisphere 182 of the passage 180 is configured to receive the second end 162 of another intermediate link 128 when the other intermediate link 128 is coupled to the given intermediate link 128.

The intermediate link 128 also defines a first through-hole 190, a second through-hole 192, and a third through-hole 194. (See FIG. 8C). The first through-hole 190 is substantially parallel to the longitudinal axis 164, extends from the first portion 166 toward the second end 162, and is positioned between the passage 180 and the first surface 170. The second through-hole 192 is substantially parallel to the longitudinal axis 164, extends from the first portion 166 to the second end 162, and is positioned between the passage 180 and the first surface 170. The third through-hole 194 is substantially parallel to the longitudinal axis 164, extends from the first portion 166 to the second end 162, and is positioned between the passage 180 and the first surface 170. The first, second and third through-holes 190, 192, 194 are generally cylindrically shaped. According to various embodiments, the through-holes 190, 192, 194 are evenly spaced from one another. The size of each of the through-holes 190, 192, 194 may be identical to one another or may be different from one another. For example, according to various embodiments, the respective diameters associated with the through-holes 190, 192, 194 may each be on the order of approximately 1.25 millimeters. The first through-hole 190 is configured to receive and surround the first cable 16. The second through-hole 192 is configured to receive and surround the second cable 18. The third through-hole 194 is configured to receive and surround the third cable 20. The first, second and third through-holes 190, 192, 194 may serve as guidepaths for movement of the first, second and third cables 16, 18, 20.

As shown in FIG. 8C, the intermediate link 128 also defines first, second and third indents 196, 198, 200 at the second end 162 thereof resulting, in part, from the combination of the taper associated with the second portion 168 and the configuration and orientation of the first, second, and third grooves 174, 176, 178. The first, second and third indents 196, 198, 200 may be evenly spaced about the second end 162 of the intermediate link 128 as shown in FIG. 8C. The first, second and third indents 196, 198, 200 may serve to reduce the pinching or binding of various tools or instruments (e.g., ablation tools) when one intermediate link 128 of the second mechanism 14 is moved relative to another intermediate link 128 coupled thereto.

The intermediate link 128 also defines fourth, fifth and sixth indents 202, 204, 206 at the second end 162 thereof resulting from the combination of the taper associated with the second portion 168 and the configuration and orientation of the first, second, and third through-holes 190, 192, 194. The fourth, fifth and sixth indents 202, 204, 206 may be evenly spaced about the second end 162 of the intermediate link 128, and may be evenly spaced from the first, second and third indents 196, 198, 200 as shown in FIG. 8C. The fourth, fifth and sixth indents 202, 204, 206 may serve to reduce the pinching or binding of the first, second and third cables 16, 18, 20 when one intermediate link 128 of the second mechanism 14 is moved relative to another intermediate link 128 coupled thereto.

According to various embodiments, an intermediate link 128 may also define an opening (not shown) that extends from the second surface 172 or from one of the grooves 174, 176, 178 to the first surface 170 of the intermediate link 128. The intermediate link 128 may have any number of such openings, and any number of the intermediate links 128 may have such openings. The opening may be utilized as an exit point for a tool or instrument which may pass from the first end 24 of the multi-linked device 10 toward the second end 26 of the multi-linked device 10. For such embodiments, the respective intermediate link 128 may be positioned proximate the second link 126 of the second mechanism 14. The opening may be oriented at any angle relative to the longitudinal axis 134 of the intermediate link 128. When the first mechanism 12 is removed from the second mechanism 14, and a relatively large tool or instrument is advanced from the first end 120 of the second mechanism 14 to the second end 122 of the second mechanism 14, sufficient room may not exist for a second tool or instrument (e.g., fiber optic cable) to pass through the second end 122 of the second mechanism 14. For such instances, the second tool or instrument may exit through an opening of one of the intermediate links 128.

With the above described structure, the first link 124 may be coupled to the intermediate link 128 by seating the second end 132 of the first link 124 in the segmented hemisphere 182 of the passage 180 of the intermediate link 128. As the convex configuration of the second end 132 of the first link 124 generally corresponds with the concave configuration of the segmented hemisphere 182 of the passage 180 of the intermediate link 128, the first link 124 may be coupled to the intermediate link 128 such that the longitudinal axis 134, the first, second and third grooves 142, 144, 146, and the first, second and third through-holes 154, 156, 158 of the first link 124 are respectively aligned with the longitudinal axis 164, the first, second and third grooves 174, 176, 178, and the first, second and third through-holes 190, 192, 194 of the intermediate link 128. The intermediate link 128 may be moved relative to the first link 124 such that the longitudinal axis 164 of the intermediate link 128 is not aligned with the longitudinal axis 134 of the first link 124. According to various embodiments, the configuration of the first link 124 and the intermediate link 128 allows for the intermediate link 128 to be moved relative to the first link 124 coupled thereto such that the longitudinal axis 134 of the first link 124 and the longitudinal axis 164 of the intermediate link 128 are up to approximately 10° out of alignment with one another. Similarly, one intermediate link 128 may be coupled to another intermediate link 128, and so on, by seating the second end 162 of one intermediate link 128 in the segmented hemisphere 182 of the passage 180 of another intermediate link 128. As the convex configuration of the second end 162 of the intermediate link 128 generally corresponds with the concave configuration of the segmented hemisphere 182 of the passage 180 of the intermediate link 128, the intermediate links 128 may be coupled such that the respective longitudinal axes 164, the respective first, second and third grooves 174, 176, 178, and the respective first, second and third through-holes 190, 192, 194 of the intermediate links 128 are aligned. The coupled intermediate links 128 may be moved relative to one another such that the respective longitudinal axes 164 of the coupled intermediate links 128 are not aligned. According to various embodiments, the configuration of the coupled intermediate links 128 allows for one intermediate link 128 to be moved relative to another intermediate link 128 coupled thereto such that the respective longitudinal axes 164 are up to approximately 10° out of alignment with one another.

Figure 9A:
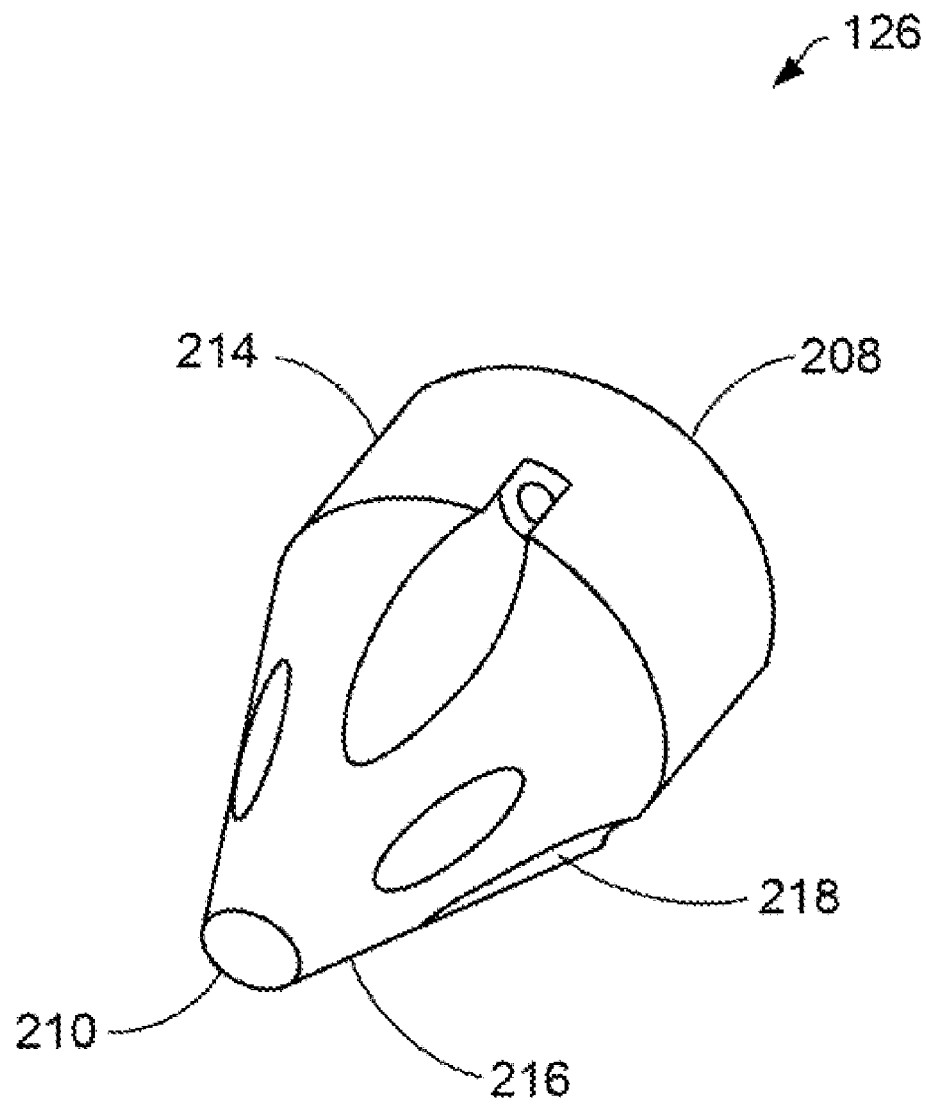
FIGS. 9A-9D illustrate various embodiments of a distal link of the sleeve mechanism.
Figure 9B:
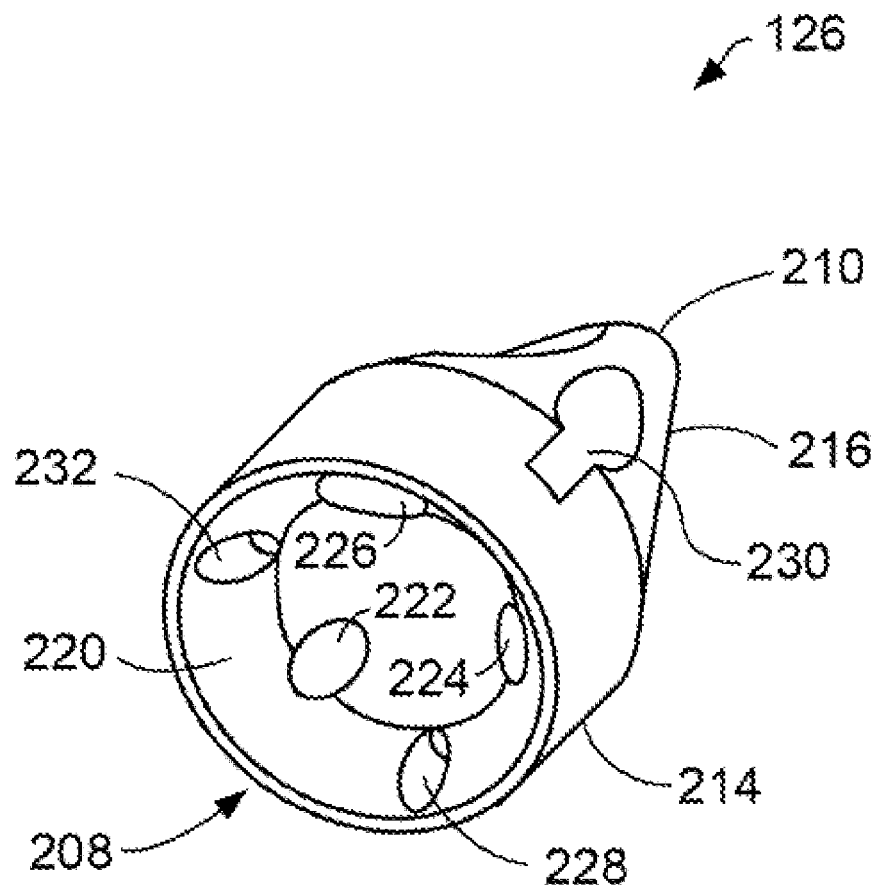
Figure 9C:
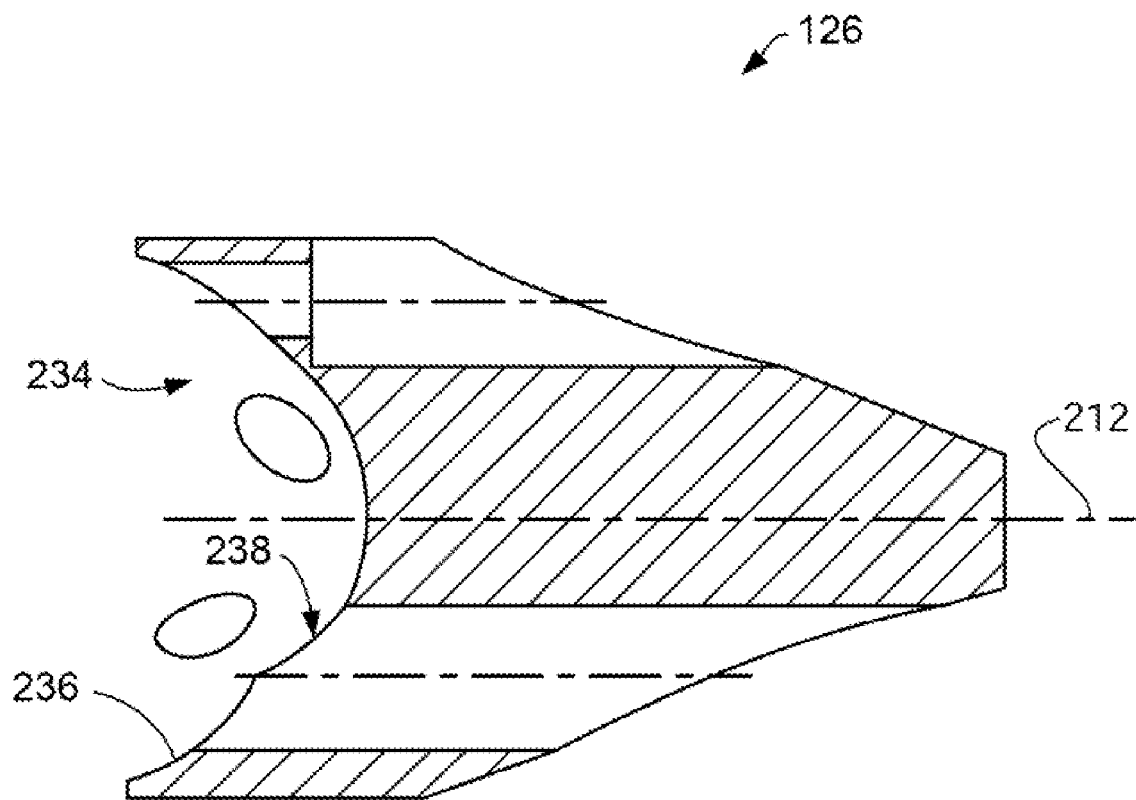

FIGS. 9A-9D illustrate various embodiments of the second link 126 (outer distal link) of the second mechanism 14. The second link 126 includes a first end 208 and a second end 210, and defines a longitudinal axis 212 that passes through the center of the first end 208 and the center of the second end 210 as shown in FIG. 9C. The second link 126 may be fabricated from any suitable material. According to various embodiments, the second link 126 is fabricated from a thermoplastic material such as, for example, Delrin®.

The second link 126 includes a first portion 214 and a second portion 216. The first portion 214 may be considered the proximal portion and the second portion 216 may be considered the distal portion. The first portion 214 may be fabricated integral with the second portion 216. The first portion 214 has a generally cylindrical shaped exterior, and extends from the first end 208 of the second link 126 toward the second end 210 of the second link 126. According to various embodiments, the diameter of the first portion 214 is on the order of approximately 4.80 millimeters.

According to various embodiments, the second portion 216 has a generally cylindrically shaped exterior where it contacts the first portion 214, and tapers toward the second end 210 of the second link 126. The exterior of the second portion 216 is configured in the form of a generally segmented cone. According to various embodiments, the exterior of the second portion 216 tapers from the first portion 214 to the second end 210 of the second link 126 at an angle on the order of approximately 20° relative to the exterior of the first portion 214. The length of the second link 126 may be on the order of approximately 15 millimeters. However, one skilled in the art will appreciate that the length of the second link 126 can vary based on the application.

The second link 126 also includes a first surface 218 that extends from the first end 208 of the second link 126 to the second end 210 of the second link 126, and a second surface 220 that extends from the first end 208 of the second link 126 toward the second end 210 of the second link 126. The first surface 218 may be considered the outer surface of the second link 126, and the second surface 220 may be considered the inner surface of the second link 126.

Figure 9D:
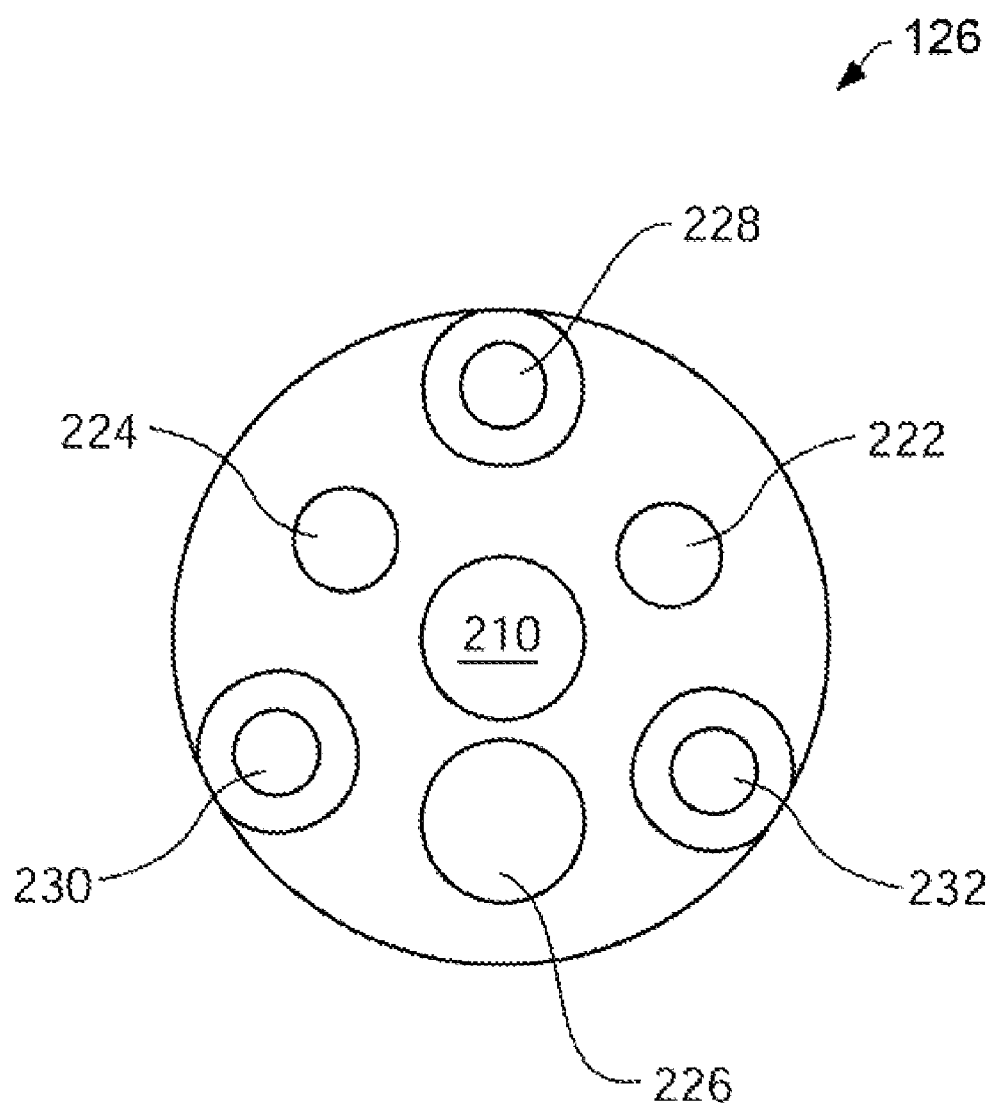

The second link 126 also defines a first port 222, a second port 224, and a third port 226. (See FIG. 9B). The first port 222 extends from the second surface 220 to the first surface 218 and is substantially parallel to the longitudinal axis 212. The second port 224 extends from the second surface 220 to the first surface 218 and is substantially parallel to the longitudinal axis 212. The third port 226 extends from the second surface 220 to the first surface 218 and is substantially parallel to the longitudinal axis 212. The first, second and third ports 222, 224, 226 may be cylindrical shaped and may be evenly spaced about the longitudinal axis 212 of the second link 126 as shown in FIG. 9D. The size of each of the ports 222, 224, 226 may identical to one another or may be different from one another. For example, according to various embodiments, the first and second ports 222, 224 are configured as cylinders having diameters on the order of approximately 1.50 millimeters, and the third port 226 is configured as a cylinder having a diameter on the order of approximately 2.50 millimeters. The first, second and third ports 222, 224, 226 are each configured to receive and surround any of a variety of tools or instruments (e.g., ablation tools) which may pass from the first end 24 of the multi-linked device 10 to the second end 26 of the multi-linked device 10.

The second link 126 also defines a first through-hole 228, a second through-hole 230, and a third through-hole 232. (See FIG. 9B). The first through-hole 228 extends from the second surface 220 to the first surface 218 and is substantially parallel to the longitudinal axis 212. The second through-hole 230 extends from the second surface 220 to the first surface 218 and is substantially parallel to the longitudinal axis 212. The third through-hole 232 extends from the second surface 220 to the first surface 218 and is substantially parallel to the longitudinal axis 212. The first, second and third through-holes 228, 230, 232 are generally cylindrically shaped. According to various embodiments, the through-holes 228, 230, 232 are evenly spaced from one another as shown in FIG. 9D. The size of each of the through-holes 228, 230, 232 may be identical to one another or may be different from one another. For example, according to various embodiments, the respective diameters associated with the through-holes 228, 230, 232 may each be on the order of approximately 1.25 millimeters. The first through-hole 228 is configured to receive and surround the first cable 16. The second through-hole 230 is configured to receive and surround the second cable 18. The third through-hole 232 is configured to receive and surround the third cable 20. As shown in FIG. 9D, each of the through-holes 228, 230, 232 may include a respective counter-bored section 228a, 230a, 232a at the distal end of the through-holes 228, 230, 232.

The second link 126 also defines a recess 234 that extends from the first end 208 toward the second end 210 along the longitudinal axis 212 as shown in FIG. 9C. According to various embodiments, the recess 234 is generally configured as a complex shape that includes a combination of a first segmented hemisphere 236 that extends from the first end 208 toward the second end 210, and a second segmented hemisphere 238 that extends from the first segmented hemisphere 236 toward the second end 210 of the second link 126. According to various embodiments, the first segmented hemisphere 236 represents a portion of a sphere having a diameter on the order of approximately 9.50 millimeters, and second segmented hemisphere 238 represents a portion of a sphere having a diameter on the order of approximately 7.0 millimeters. The first segmented hemisphere 236 of the recess 234 is configured to receive the second end 162 of an intermediate link 128 when the intermediate link 128 is coupled to the second link 126.

With the above described structure, an intermediate link 128 may be coupled to the second link 126 by seating the second end 162 of the intermediate link 128 in the first segmented hemisphere 236 of the recess 234 of the second link 126. As the convex configuration of the second end 162 of the intermediate link 128 generally corresponds with the concave configuration of the first segmented hemisphere 236 of the recess 234 of the second link 126, the inter-mediate link 128 may be coupled to the second link 126 such that the longitudinal axis 164, the first, second and third grooves 174, 176, 178, and the first, second and third through-holes 190, 192, 194 of the intermediate link 128 are respectively aligned with the longitudinal axis 212, the first, second and third ports 222, 224, 226, and the first, second and third through-holes 228, 230, 232 of the second link 126. The second link 126 may be moved relative to the intermediate link 128 coupled thereto such that the respective longitudinal axes 164, 212 are not aligned. According to various embodiments, the configuration of the second link 126 allows for an intermediate link 128 coupled thereto to be moved relative to the second link 126 such that the respective longitudinal axes 164, 212 are up to approximately 10° out of alignment with one another.

When the first mechanism 12 is inserted into the second mechanism 14, the first second and third grooves 70, 72, 74 of the intermediate links 32 of the first mechanism 12 may be substantially aligned with the first, second and third grooves 174, 176, 178 of the intermediate links 128 of the second mechanism 14, and the first, second and third grooves 98, 100, 102 of the second link 30 of the first mechanism 12 may be substantially aligned with the first, second and third ports 222, 224, 226 of the second link 126 of the second mechanism 14. The combination of the first grooves 70 of the intermediate links 32 of the first mechanism 12 aligned with the first grooves 174 of the intermediate links 128 of the second mechanism 14 allows the respective first grooves 70, 174 to collectively serve as a first working port that is substantially aligned with the first port 222 of the second link 126 of the second mechanism 14. As used herein, the term "working port" means a passageway through which a device (e.g., a camera, a fiber optic, an ablation tool, a surgical instrument, etc.) can pass. The first groove 70 may be considered the inner portion of the first working port and the first groove 174 may be considered the outer portion of the first working port.

Similarly, the combination of the second grooves 72 of the intermediate links 32 of the first mechanism 12 aligned with the second grooves 176 of the intermediate links 128 of the second mechanism 14 allows the respective second grooves 72, 176 to collectively serve as a second working port that is substantially aligned with the second port 224 of the second link 126 of the second mechanism 14, and the combination of the third grooves 74 of the intermediate links 32 of the first mechanism 12 aligned with the third grooves 178 of the intermediate links 128 of the second mechanism 14 allows the respective third grooves 74, 178 to collectively serve as a third working port that is substantially aligned with the third port 226 of the second link 126 of the second mechanism 14. The second groove 72 may be considered the inner portion of the second working port and the second groove 176 may be considered the outer portion of the second working port. The third groove 74 may be considered the inner portion of the third working port and the third groove 178 may be considered the outer portion of the third working port. The first, second and third working ports may be utilized to pass various tools or instruments (e.g., ablation tools) from the first end 24 of the multi-linked device 10 to the second end 26 of the multi-linked device 10. For the exemplary sizes described hereinabove, the third working port is larger than the first and second working ports. Accordingly, the third working port may be utilized to carry a particular tool or instrument that is too large to be carried by the first or second working ports.

When the respective grooves 70, 72, 74, 174, 176, 178 of the respective intermediate links 32, 128 are aligned and collectively surround the various tools and instruments, the combination of the grooves 70, 72, 74, 174, 176, 178 and the tools and instruments may serve to limit or prevent the rotation of the first mechanism 12 relative to the second mechanism 14.

As the diameter of the passage 180 of the intermediate link 128 of the second mechanism 14 is larger than the diameter of any portion of the first mechanism 12, a three-dimensional space 240 exists between the first mechanism 12 and the second mechanism 14 when the first mechanism 12 is received by the second mechanism 14 (See FIG. 1B). According to various embodiments, the space 240 may be utilized to carry wiring, tools, instruments, etc. from the first end 24 of the multi-linked device 10 toward the second end 26 of the multi-linked device 10.

The first, second and third cables 16, 18, 20 may be fabricated from any suitable material. For example, according to various embodiments, the cables 16, 18, 20 may be fabricated from a polyethylene fiber cable such as, for example, Spectra®. The cables 16, 18, 20 may be utilized to control the movement of the multi-linked device 10. For example, by applying a substantially equal tension to each of the cables 16, 18, 20, the first mechanism 12 and/or second mechanism 14 may be steered in a direction such that the respective longitudinal axes 38, 62, 90, 134, 164, 212 of each of the links 28, 30, 32, 124, 126, 128 are all aligned. By applying a different tension to one or more of the cables 16, 18, 20, the first mechanism 12 and/or the second mechanism 14 may be steered in a direction such that the respective longitudinal axes 38, 62, 90, 134, 164, 212 of each of the links 28, 30, 32, 124, 126, 128 are not all aligned. The cables 16, 18, 20 may also be utilized to control the relative state of the second mechanism 14. For example, when a uniform tension is applied to the cables 16, 18, 20, the second mechanism 14 is placed in a "rigid" state, and when a tension is removed from the cables 16, 18, 20, the second mechanism 14 is placed in a "limp" state. According to various embodiments, the cables 16, 18, 20 may be attached at the first end 130 of the first link 124 of the second mechanism 14 to respective pullies (not shown) by, for example, respective stopper knots. The cables 16, 18, 20 may be attached to the second end 132 of the second link 126 of the second mechanism 14 by, for example, respective stopper knots positioned in the counter-bored sections 228a, 230a, 232a of the second link 126. One skilled in the art will appreciate that, according to other embodiments, the "rigid" and "limp" states may be achieved by subjecting the first and/or second mechanisms 12, 14 to a twisting force, or by any other manner known in the art.

The fourth cable 22 may be fabricated from any suitable material. For example, according to various embodiments, the cable 22 may be fabricated from a polyethylene fiber cable such as, for example, Spectra®. The fourth cable 22 may be utilized to control the relative state of the first mechanism 12. For example, when the fourth cable 22 is drawn tight, the first mechanism 12 is placed in a "rigid" state, whereas when the fourth cable 22 is let loose, the first mechanism 12 is placed in a "limp" state. According to various embodiments, the fourth cable 22 may be attached at the first end 34 of the first link 28 of the first mechanism 12 to a pulley (not shown) by, for example, a stopper knot. The fourth cable 22 may be attached to the second end 88 of the second link 30 of the first mechanism 12 by, for example, a stopper knot.

Figure 10:
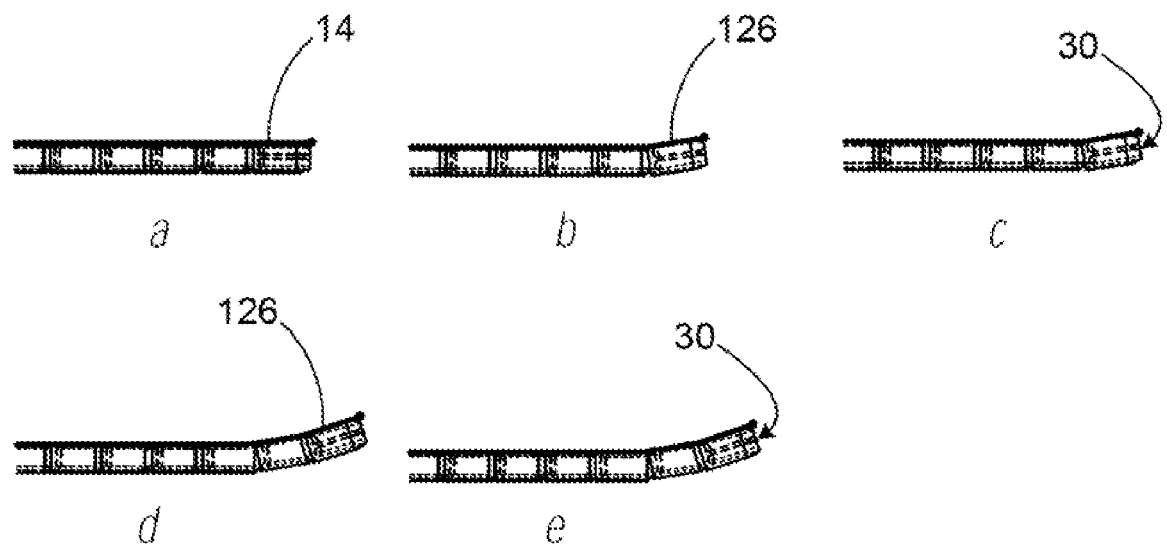
FIG. 10 illustrates various embodiments of a motion sequence of the device of FIG. 1.

FIG. 10 illustrates various embodiments of a motion sequence of the steerable multi-linked device 10. At the start of the sequence, the second mechanism 14 surrounds the first mechanism 12 as shown in step "a" of FIG. 10, the longitudinal axes 38, 62, 90 of the links 28, 30, 32 of the first mechanism 12 are substantially aligned with the respective longitudinal axes 134, 164, 212 of the links 124, 126, 128 of the second mechanism, and the second end 26 of the first mechanism 12 is at substantially the same position as the second end 122 of the second mechanism 14. The fourth cable is pulled tight, thereby placing the first mechanism 12 in the rigid mode. The cables 16, 18, 20 are not pulled tight, thereby placing the second mechanism 14 in the limp mode.

The second mechanism 14 is then advanced so that its second link 126 is positioned approximately one link ahead of the second end 24 of the first mechanism 12 as shown in step "b" of FIG. 10. The cables 16, 18, 20 may be utilized to orient the second link 126 to a particular orientation, where the longitudinal axis 134 of the first link 124 is no longer aligned with the longitudinal axes 164 of the intermediate links 128 of the second mechanism 14 or the longitudinal axis 90 of the second link 30 of the first mechanism 12. After the second link 126 is in the desired position and orientation, the cables 16, 18, 20 are pulled with identical force in order to place the second mechanism 14 in the rigid mode, thereby preserving the position and orientation of the second mechanism 14.

The pulling force of the fourth cable 22 is then released to place the first mechanism 12 the limp mode. After the first mechanism 12 is placed in the limp mode, the first mechanism 12 is advanced so that its second link 30 is at substantially the same position as the second end 122 of the second mechanism 14 as shown in step "c" of FIG. 10. After the second link 30 of the first mechanism 12 is in the desired position and orientation, the fourth cable 22 is pulled tight to place the first mechanism 12 back in the rigid mode, thereby preserving the position and orientation of the first mechanism 12.

The pulling forces of the cables 16, 18, 20 are then released to place the second mechanism 14 back in the limp mode.

After the second mechanism 14 is placed back in the limp mode, the second mechanism 14 is advanced so that its second link 126 is once again positioned approximately one link ahead of the second end 26 of the first mechanism 12 as shown in step "d" of FIG. 10. After the second link 126 is in the desired position and orientations the cables 16, 18, 20 are pulled with identical force in order to place the second mechanism 14 in the rigid mode, thereby preserving the position and orientation of the second mechanism 14.

The pulling force of the fourth cable 22 is then released to place the first mechanism 12 back in the limp mode. After the first mechanism 12 is placed back in the limp mode, the first mechanism 12 is advanced so that its second link 30 is once again at substantially the same position as the second end 122 of the second mechanism 14 as shown in step "e" of FIG. 10. After the second link 30 of the first mechanism 12 is in the desired position and orientation, the fourth cable 22 is pulled tight to place the first mechanism 12 back in the rigid mode, thereby preserving the position and orientation of the first mechanism 12. The general motion sequence described hereinabove, may be repeated any number of times, and the second link 126 of the second mechanism 14 may be advancing in any direction and orientation. One skilled in the art will appreciate that any number of motion sequences may be utilized with the multi-linked device 10. For example, according to various embodiments, the second mechanism 14 may advance any number of links ahead of the first mechanism 12.

The exemplary sizes described hereinabove are generally relative to each other, and one skilled in the art will appreciate that the multi-linked device 10 can be scaled up or scaled down. For example, although the diameter at the largest portion of the intermediate link 128 of the multi-linked device 10 is on the order of approximately 9.65 millimeters for the embodiments described hereinabove, one skilled in the art will appreciate that, for other embodiments, the intermediate link 128 can be scaled down such that the diameter at the largest portion of the intermediate link 128 of the multi-linked device 10 is on the order of approximately 1.0 millimeter. For such embodiments, each of the other components of the multi-linked device 10 would also be proportionally scaled down.

Figure 11:
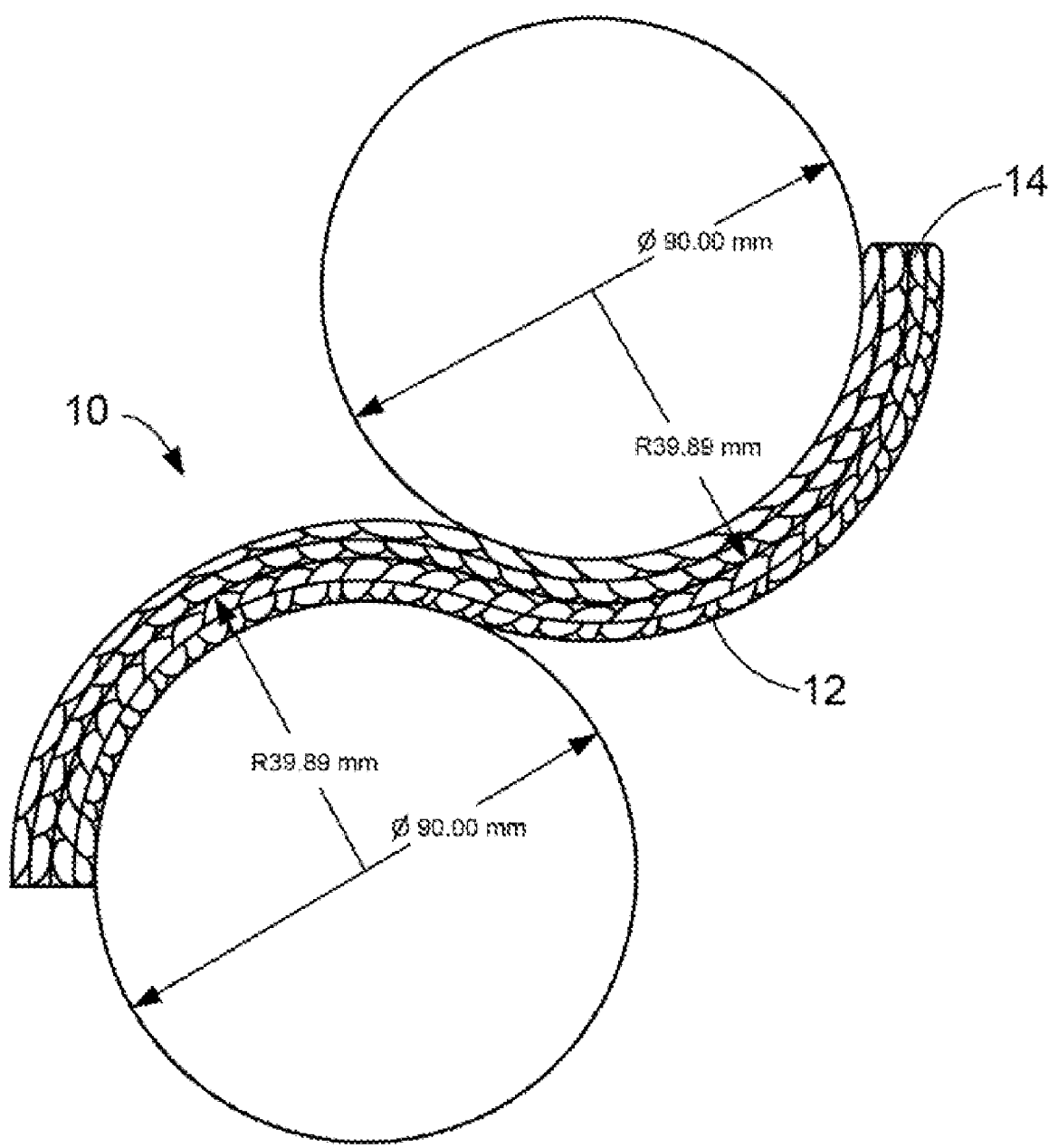
FIG. 11 illustrates various embodiments of a steerable multi-linked device traversing a path having tight curvatures.

The combination of the unique configuration of the respective links 28, 30, 32 which comprise the first mechanism 12 and the unique configuration of the respective links 124, 126, 128 which comprise the second mechanism 14 provides the multi-linked device 10 with the ability to traverse a path defined by the circumference of a circle having a relatively small radius. For example, for the exemplary sizes described hereinabove, the multi-linked device 10 can traverse a path defined by the circumference of a circle having a radius on the order of approximately 40 millimeters. An example of the multi-linked device 10 navigating such tight curvatures is shown in FIG. 11. For embodiments where the outer diameter of the multi-linked device 10 is on the order of approximately 1.0 millimeter, the multi-linked device 10 can traverse a path defined by the circumference of a circle having the radius on the order of approximately 4.0 millimeters. Stated differently, the multi-linked device 10 can traverse a path defined by circumference of a circle having a radius which is approximately only four times the outer diameter of the device. One skilled in the art will appreciate that the ability to navigate such tight curvatures makes the multi-linked device 10 suitable for use in a number of different minimally invasive procedures, both in luminal spaces and in intracavity spaces.

Figure 12A:
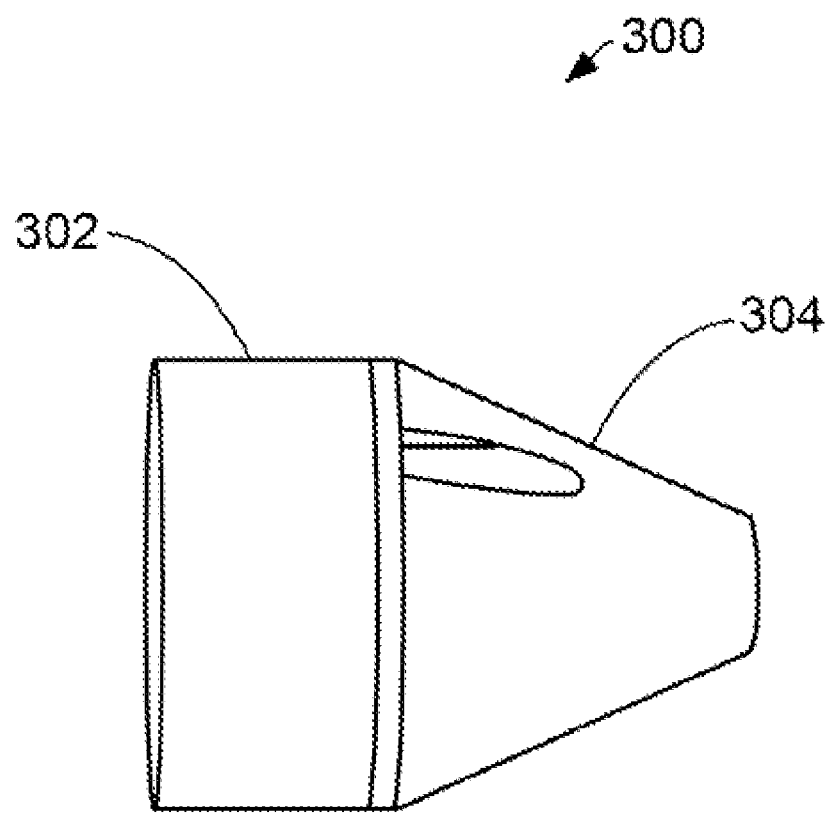
FIGS. 12A-12C illustrate various embodiments of a modular link assembly for a multi-linked device.
Figure 12B:
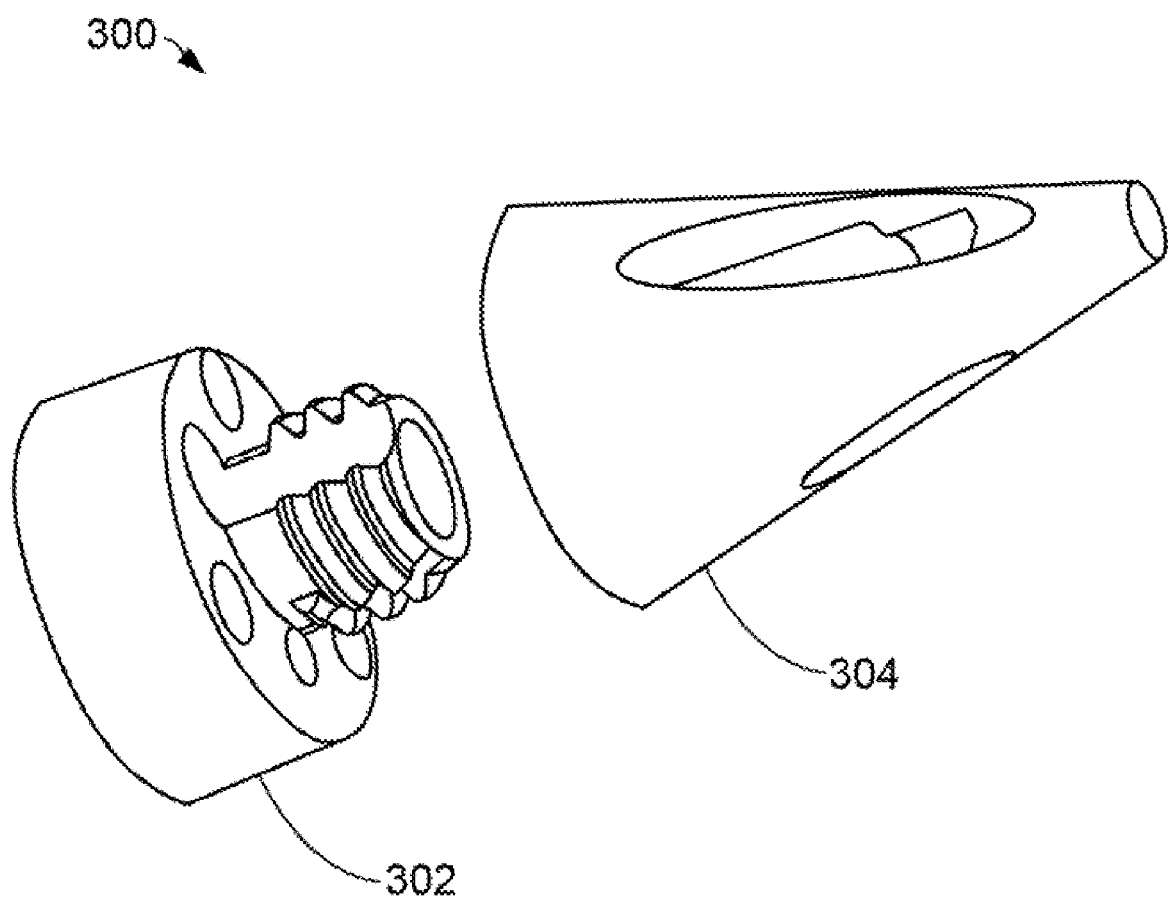
Figure 12C:
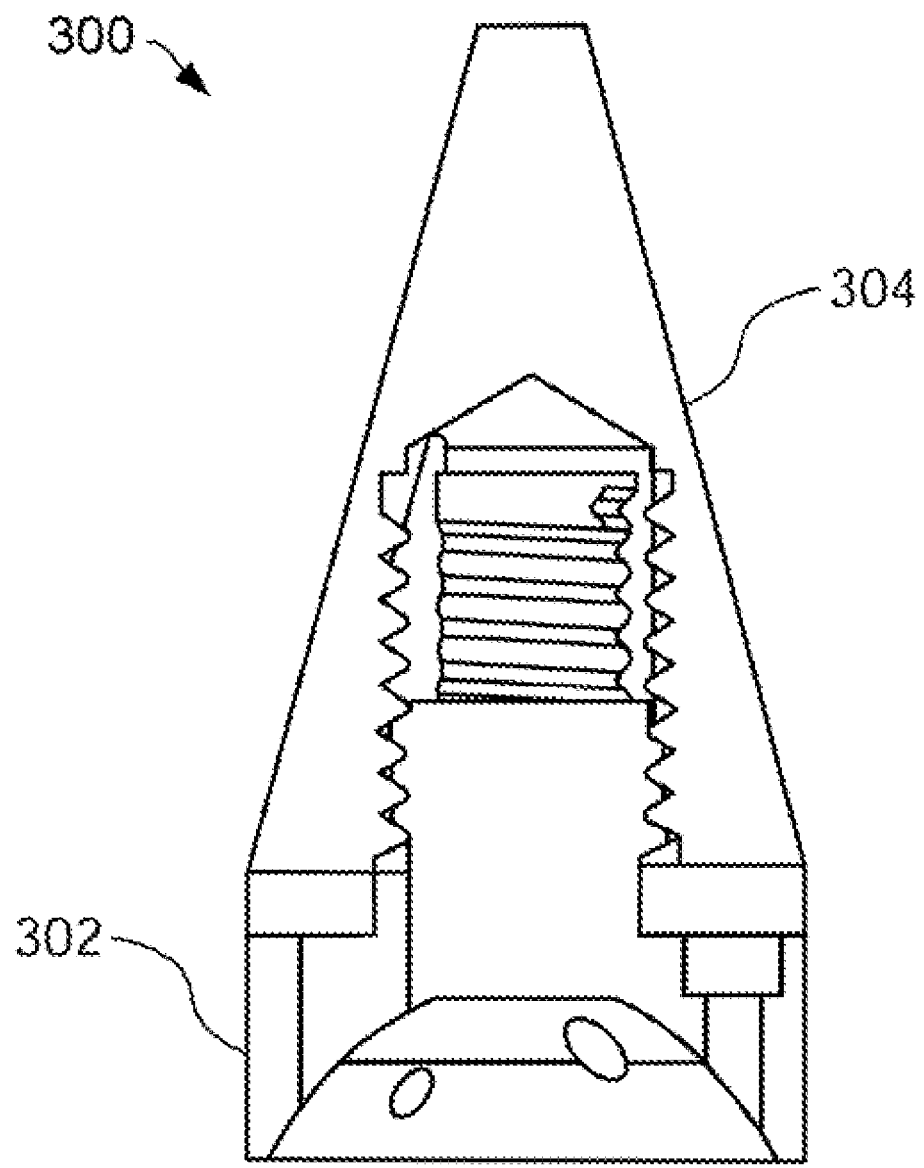

FIGS. 12A-12C illustrate various embodiments of the modular link assembly 300. When utilized with the steerable multi-linked device 10 described hereinabove, the modular link assembly 300 may replace the second link 126 of the second mechanism 14, and may thus serve as the distal link of the second mechanism 14. The modular link assembly 300 includes a base 302, and a tip 304 removably connected to the base 302. The link assembly 300 may be considered "modular" in that a variety of different tips 304 may be connected to and removed from the base 302. The specific type of tip 304 utilized at a given point in time may vary depending on the particular application.

The tip 304 is shown connected to the base 302 in FIG. 12A, and is shown removed from the base 302 in FIG. 12B. The tip 304 may be removably connected to the base 302 in any suitable manner. According to various embodiments, the tip 304 may be threadedly connected to the base 302 as shown in FIG. 12C. According to other embodiments, the tip 304 may be connected to the base 302 via a snap-fit or any other suitable connection. Those skilled in the art will appreciate that a variety of different connection types may be utilized to connect the tip 304 to the base 302. By way of example, the modular link assembly 300 will be described for embodiments where the tip 304 is removably connected to the base 302 via a threaded connection. However, those skilled in the art will appreciate that the tip 304 may be removably connected to the base 302 in any suitable manner.

Figure 13A:
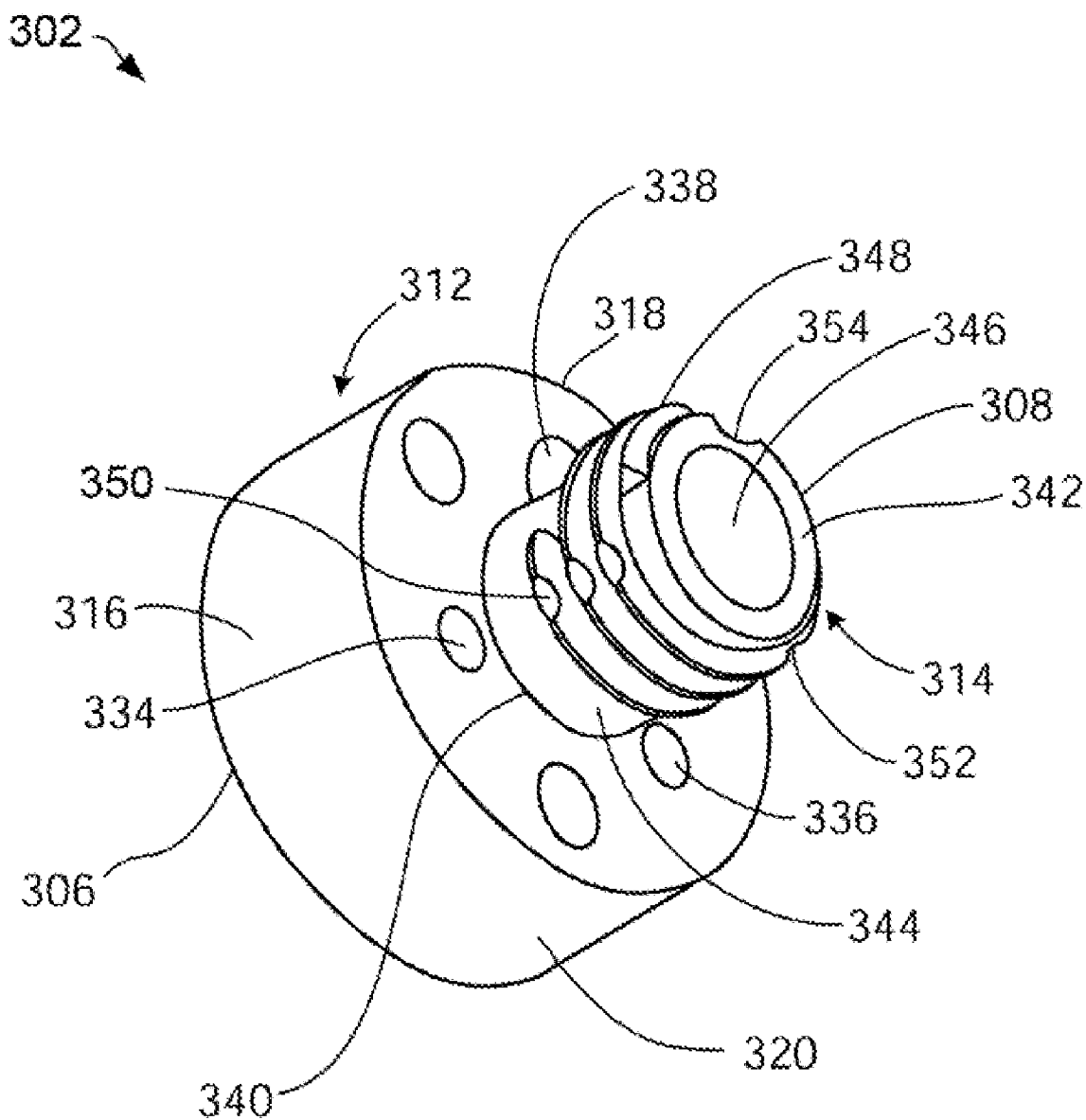
FIGS. 13A-13C illustrate various embodiments of a base of the modular link assembly of FIG. 12A.
Figure 13B:
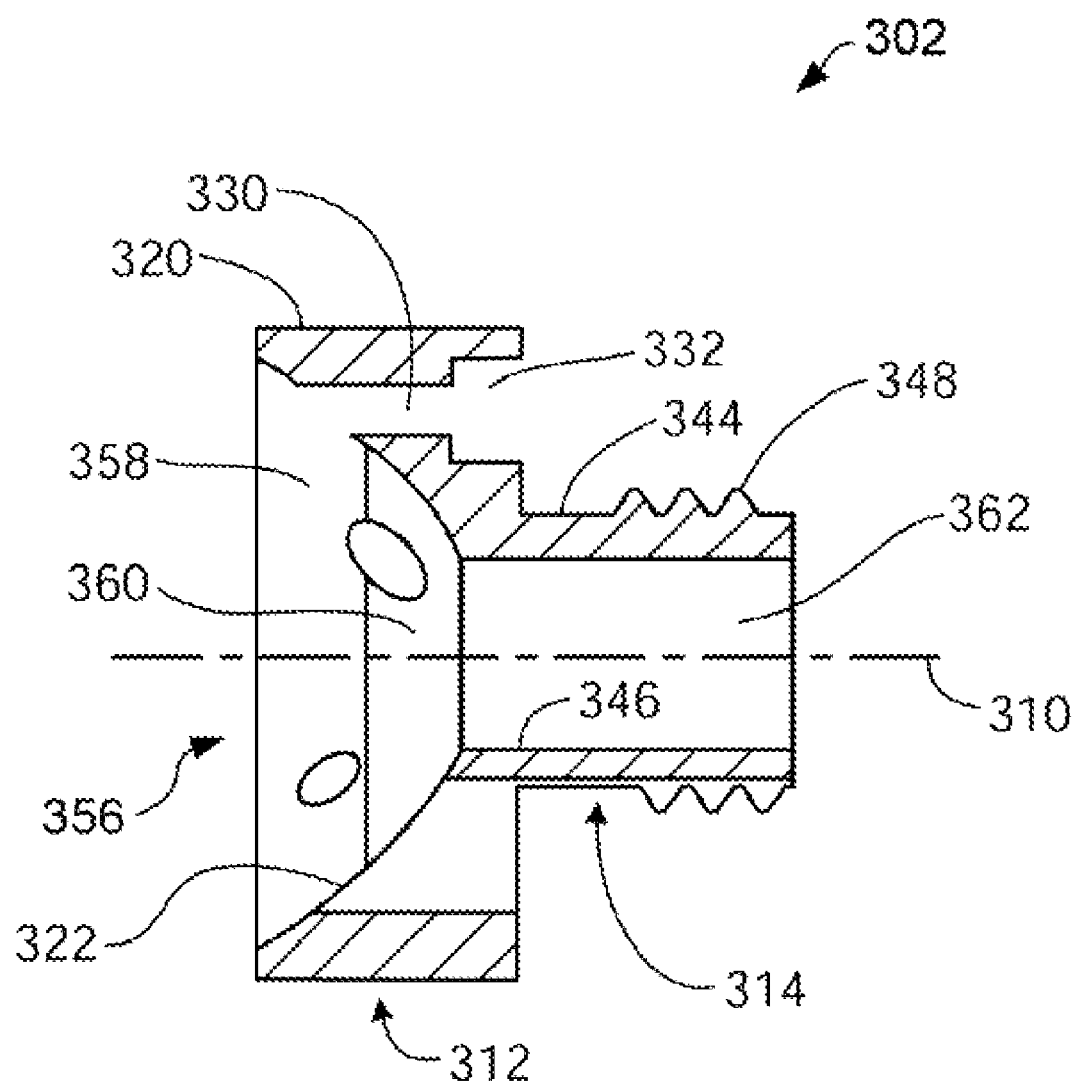
Figure 13C:
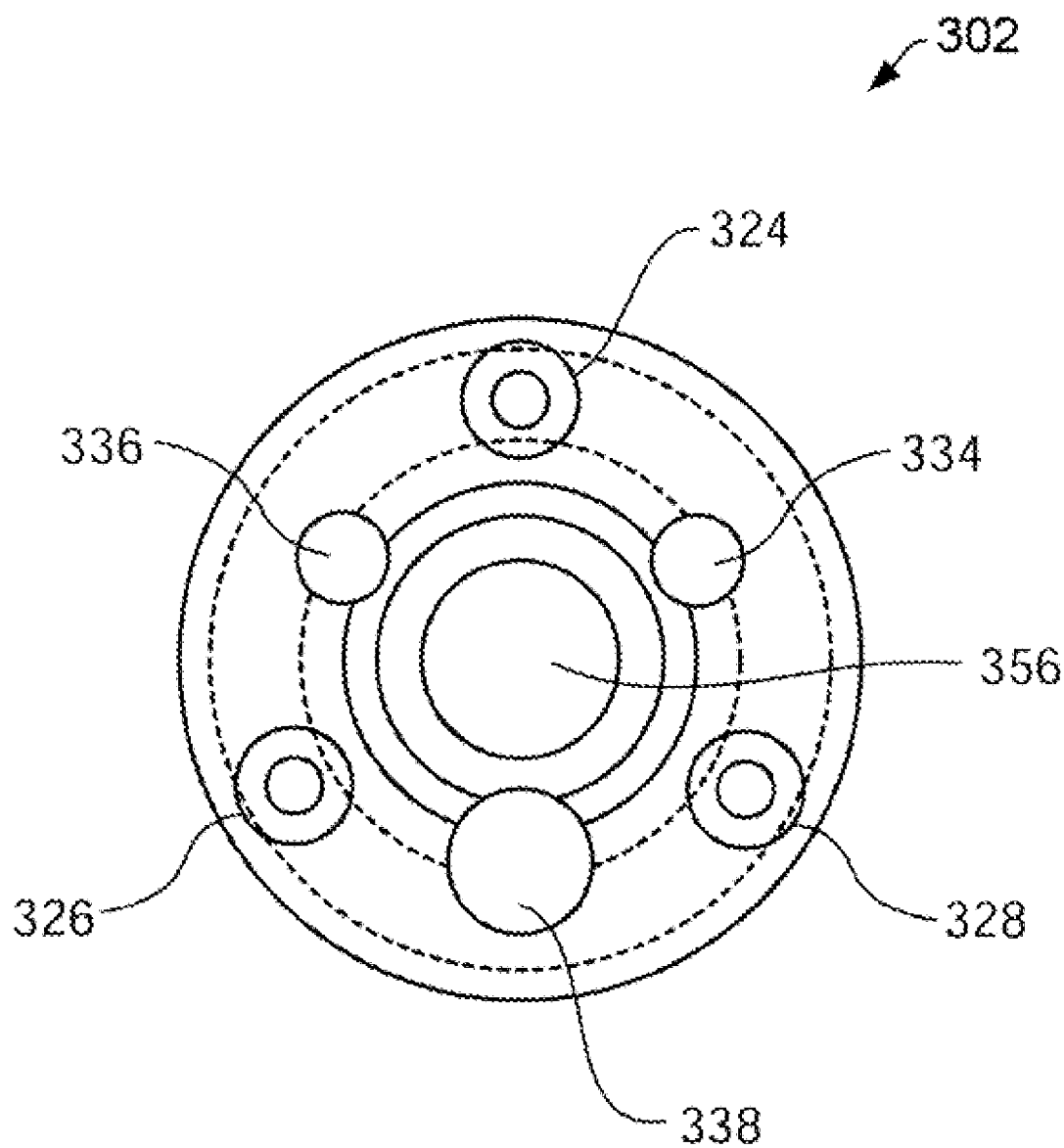

FIGS. 13A-13C illustrate various embodiments of the base 302 of the modular link assembly 300. The base 302 includes a first end 306 and a second end 308, and defines a longitudinal axis 310 that passes through the center of the first end 306 and the center of the second end 308 as shown in FIG. 13B. The base 302 may be fabricated from any suitable material. According to various embodiments, the base 302 is fabricated from a thermoplastic material such as, for example, Delrin®. According to other embodiments, the base 302 may be fabricated from, for example, an inert metal.

The base 302 includes a first portion 312, and a second portion 314 connected to the first portion 312. According to various embodiments, the first portion 312 may be formed integral with the second portion 314. The first portion 312 includes a first end 316 and a second end 318, extends from the first end 306 of the base 302 toward the second end 308 of the base 302, and has a generally cylindrical shaped exterior. According to various embodiments, the diameter of the first portion 312 is on the order of approximately 9.65 millimeters, and the length of the first portion 312 is on the order of approximately 3.85 millimeters. However, one skilled in the art will appreciate that the diameter and length of the first portion 312 can vary based on the application. The first portion 312 also includes a first surface 320 and a second surface 322. (See FIG. 13B). The first surface 320 may be considered the outer surface of the first portion 312, and the second surface 322 may be considered the inner surface of the first portion 312.

The first portion 312 of the base 302 defines a first through-hole 324, a second through-hole 326, and a third through-hole 328. (See FIG. 13C). Each of the through-holes 324, 326, 328 are substantially parallel to the longitudinal axis 310, and include a first section 330 that extends from the second surface 322 toward the second end 318 of the first portion 312, and a second section 332 that extends from the first section 330 to the second end 318 of the first portion 312. (See FIG. 13B). The respective second sections 332 may be considered counter-bored sections. Each of the first and second sections 330, 332 of the first, second and third through-holes 324, 326, 328 may be cylindrically shaped, and may be evenly spaced about the longitudinal axis 310 of the base 302 as shown in FIG. 13C. The size of each of the first sections 330 may be identical to one another or may be different from one another.

For example, according to various embodiments, the respective diameters associated with the first sections 330 may each be on the order of approximately 1 millimeter. Similarly, the size of each of the second sections 332 may be identical to one another or may be different from one another. For example, according to various embodiments, the respective diameters associated with the second sections 332 may each be on the order of approximately 2 millimeters. The first through-hole 324 is configured to receive and surround the first cable 16 of the multi-linked device 10. The second through-hole 326 is configured to receive and surround the second cable 18 of the device 10. The third through-hole 328 is configured to receive and surround the third cable 20 of the device 10.

According to various embodiments, the first portion 312 also defines a first port 334, a second port 336, and a third port 338. (See FIG. 13C). The first port 334 extends from the second surface 322 of the first portion 312 to the second end 318 of the first portion 312, and is substantially parallel to the longitudinal axis 310. The second port 336 extends from the second surface 322 of the first portion 312 to the second end 318 of the first portion 312, and is substantially parallel to the longitudinal axis 310. The third port 338 extends from the second surface 322 of the first portion 312 to the second end 318 of the first portion 312, and is substantially parallel to the longitudinal axis 310. The first, second and third ports 334, 336, 338 may be cylindrical shaped and may be evenly spaced about the longitudinal axis 310 of the base 302 as shown in FIG. 13C. The size of each of the ports 334, 336, 338 may identical to one another or may be different from one another. For example, according to various embodiments, the first and second ports 334, 336 are configured as cylinders having diameters on the order of approximately 1.50 millimeters, and the third port 338 is configured as a cylinder having a diameter on the order of approximately 2.50 millimeters. The first, second and third ports 334, 336, 338 are each configured to receive and surround any of a variety of tools or instruments (e.g. ablation tools) which may pass from the first end 24 of the multi-linked device 10 toward the second end 26 of the multi-linked device 10.

The second portion 314 of the base 302 includes a first end 340 and a second end 342, extends from the second end 318 of the first portion 312 to the second end 308 of the base 302, and has a generally cylindrically shaped exterior. According to various embodiments, the diameter of the second portion 314 is on the order of approximately 5 millimeters, and the length of the second portion 314 is on the order of approximately 4 millimeters. However, one skilled in the art will appreciate that the diameter and length of the second portion 314 can vary based on the application. The second portion 314 also includes a first surface 344 and a second surface 346. The first surface 344 may be considered the outer surface of the second portion 314, and the second surface 346 may be considered the inner surface of the second portion 314. As shown in FIGS. 13A and 133B, the first surface 344 of the second portion 314 may define a plurality of threads 348.

According to various embodiments, the threads 348 may define first, second and third grooves 350, 352, 354 which are respectively aligned with the first, second and third ports 334, 336, 338 (See FIG. 13A). Thus, the first, second and third grooves 350, 352, 354 are also evenly spaced about the longitudinal axis 310 of the base 302. As explained herein below, the grooves 350, 352 354 may cooperate with grooves defined by an interior surface of the tip 304 to form ports aligned with the first, second and third ports 334, 336, 338 of the first portion 312.

Collectively, the first and second portions 312, 314 also define a passage 356 that extends from the first end 306 of the base 302 to the second end 308 of the base 302 along the longitudinal axis 310 as shove in FIG. 13B. According to various embodiments, the passage 356 is generally configured as a complex shape that includes a combination of a first segmented hemisphere 358 that extends from the first end 306 toward the second end 308, a second segmented hemisphere 360 that extends from the first segmented hemisphere 358 toward the second end 308, and a cylinder 362 that extends from the second segmented cylinder 360 to the second end 308 of the base 302. According to various embodiments, the first segmented hemisphere 358 represents a portion of a sphere having a diameter on the order of approximately 9.65 millimeters, the second segmented hemisphere 360 represents a portion of a sphere having a diameter on the order of approximately 8.0 millimeters, and the cylinder has a diameter on the order of approximately 2.85 millimeters. The first segmented hemisphere 358 of the passage 356 is configured to receive the second end 162 of an intermediate link 128 of the multi-linked device 10 when the intermediate link 128 is coupled to the base 302.

With the above described structure, the most distal intermediate link 128 may he coupled to the base 302 by seating the second end 162 of the most distal intermediate link 128 in the first segmented hemisphere 358 of the passage 356 of the base 302. As the convex configuration of the second end 162 of the most distal intermediate link 128 generally corresponds with the concave configuration of the first segmented hemisphere 358 of the passage 356 of the base 302, the most distal intermediate link 128 may be coupled to the base 302 such that the longitudinal axis 164, the first, second and third grooves 174, 176, 178, and the first, second and third through-holes 190, 192, 194 of the most distal intermediate link 128 are respectively aligned with the longitudinal axis 310, the first, second and third ports 334, 336, 338, and the first, second and third through-holes 324, 326, 328 of the base 302. The base 302 may be moved relative to the intermediate link 128 coupled thereto such that the respective longitudinal axes 164, 310 are not aligned. According to various embodiments, the configuration of the base 302 allows for an intermediate link 128 coupled thereto to be moved relative to the base 302 such that the respective longitudinal axes 164, 310 are up to approximately 10° out of alignment with one another. According to various embodiments, the base 302 may be permanently coupled to the most distal intermediate link 128 via the cables 16, 18, 20 which pass through the most distal intermediate link 128. For example, the cables 16, 18, 20 may be attached to the base 302 of the modular link assembly 300 by, for example, respective stopper knots positioned in the second sections 332 (counter-bored sections) of the base 302. By controlling the tension placed on each of the cables 16, 18, 20, the cables 16, 18, 20 may be utilized to control the movement of the base 302 relative to the most distal intermediate link 128.

Figure 14A:
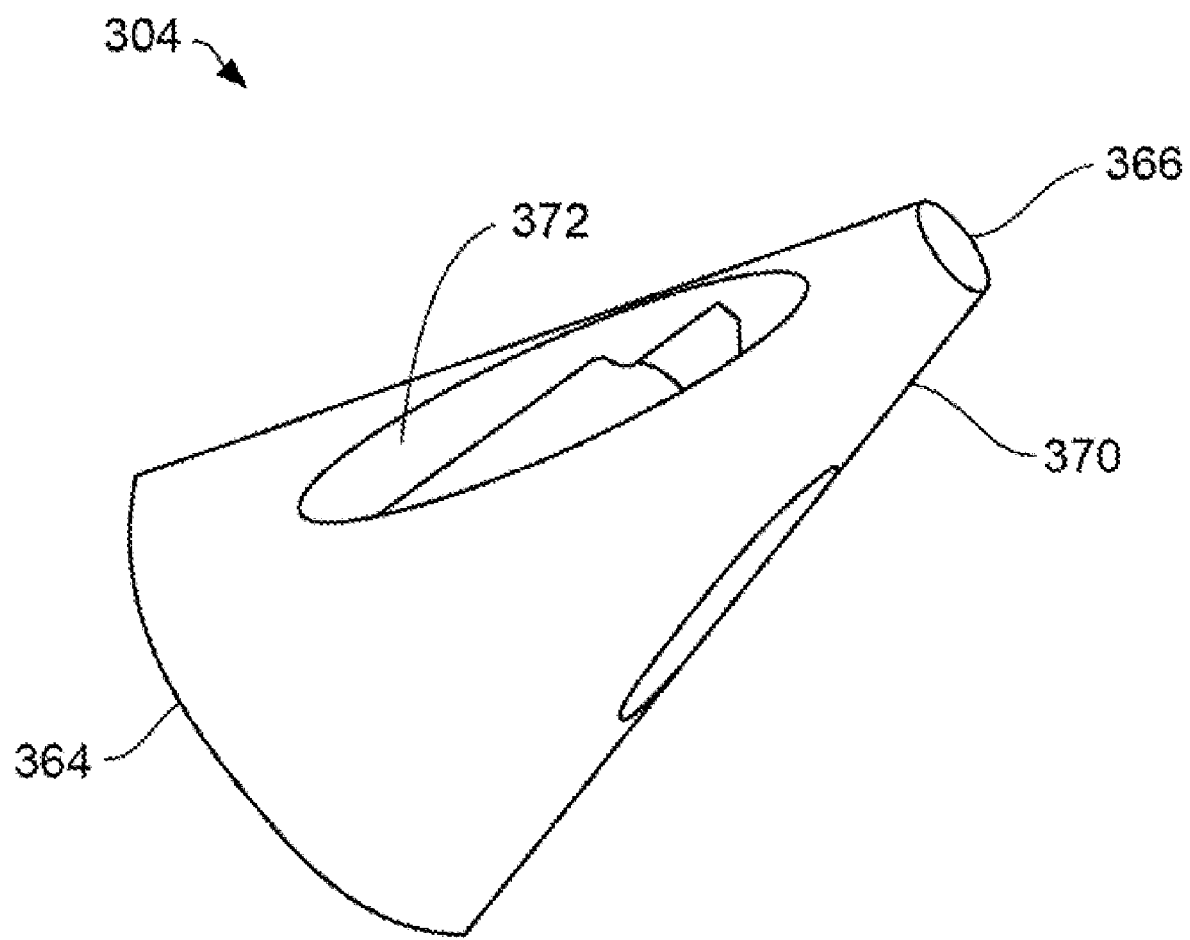
FIGS. 14A-14D illustrate various embodiments of a tip of the modular link assembly of FIG. 12A.
Figure 14B:
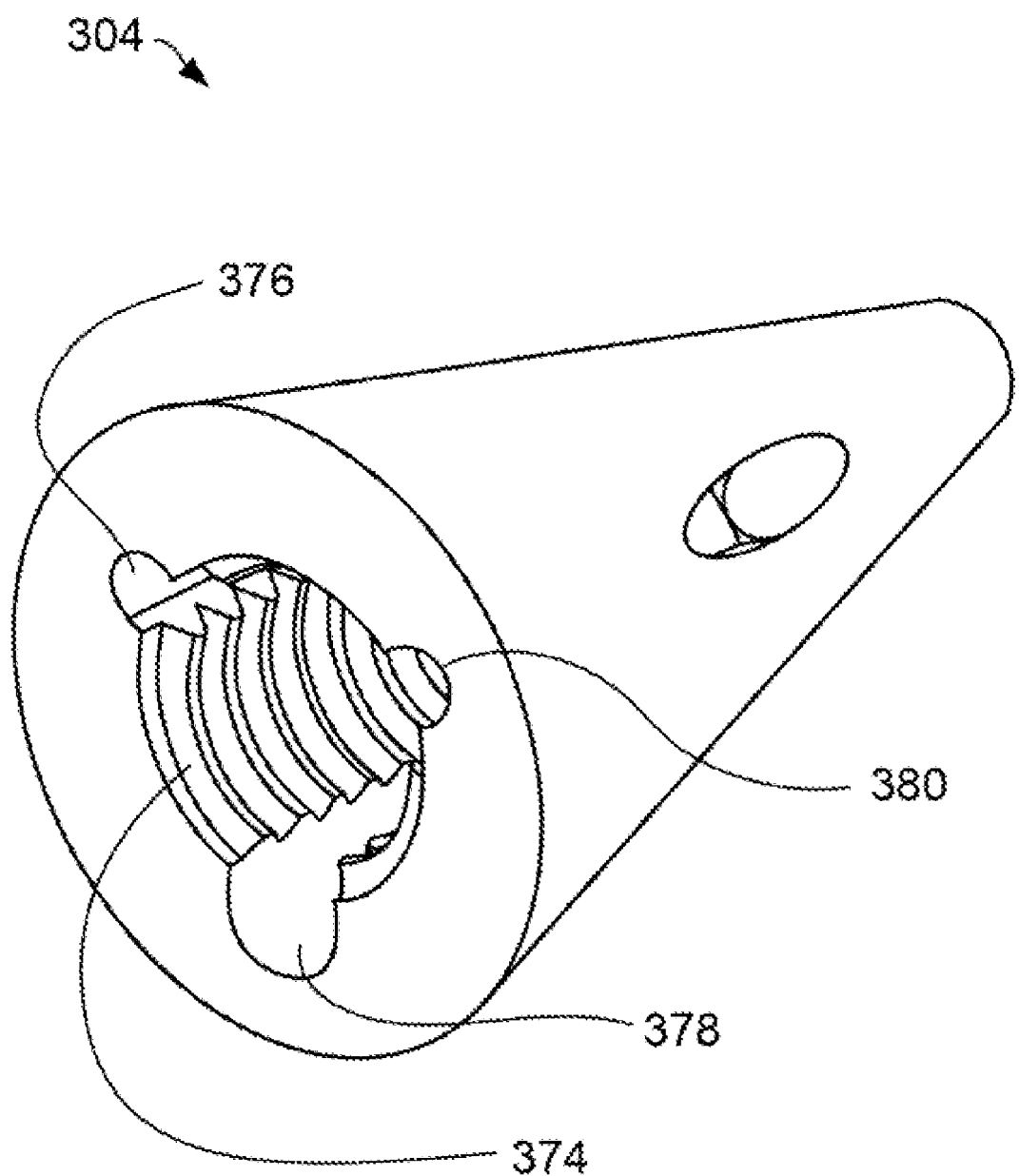
Figure 14C:
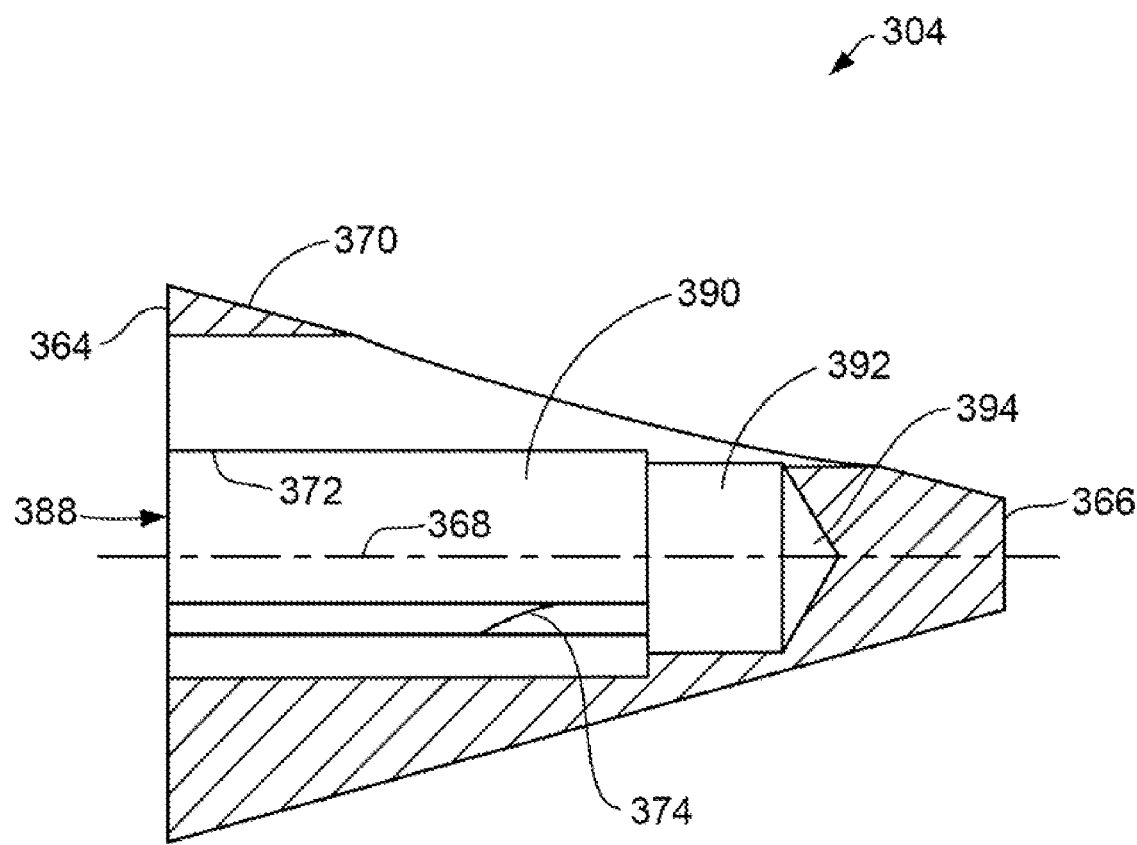

FIGS. 14A-14D illustrate various embodiments of the tip 304 of the modular link assembly 300. The tip 304 includes a first end 364 and a second end 366, and defines a longitudinal axis 368 that passes through the center of the first end 364 and the center of the second end 366 as shown in FIG. 14C. The tip 304 may be fabricated from any suitable material. According to various embodiments, the tip 304 is fabricated from a thermoplastic material such as, for example, Delrin®.

The exterior of the tip 304 is configured in the form of a generally segmented cone, and tapers from the first end 364 toward the second end 366 thereof. According to various embodiments, the exterior of the tip 304 tapers from the first end 364 to the second end 366 at an angle on the order of approximately 15° relative to the longitudinal axis 368.

According to various embodiments, the diameter of the tip 304 at the first end 364 is on the order of approximately 9.65 millimeters, the diameter of the tip 304 at the second end 366 is on the order of approximately 3.33 millimeters, and the length of the tip 304 is on the order of approximately 14.5 millimeters. However, one skilled in the art will appreciate that the respective diameters and the length of the tip 304 can vary based on the application.

The tip 304 also includes a first surface 370 that extends from the first end 364 to the second end 366 thereof, and a second surface 372 that extends from the first end 364 toward the second end 366 thereof. The first surface 370 may be considered the outer surface of the tip 304, and the second surface 372 may be considered the inner surface of the tip 304.

As shown in FIG. 14B, the second surface 372 may define a plurality of threads 374 which are structured and arranged to cooperate with the threads 348 of the base 302 to threadably connect the tip 304 to the base 302. The second surface 372 may also define first, second and third grooves 376, 378, 380 which may be evenly spaced about the longitudinal axis 368 of the tip 304 and may be respectively aligned with the first, second and third grooves 350, 352, 354 of the base 302 when the tip 304 is threadedly connected to the base 302. As explained hereinabove, the grooves 376, 378, 380 may cooperate with grooves 350, 352, 354 to form portions of first, second and third ports 382, 384, 386 (See FIG. 14D) which may be respectively aligned with the first, second and third ports 334, 336, 338 of the first portion 312 of the base 302 when the tip 304 is threadedly connected to the base 302. Other portions of the first, second and third ports 382, 384, 386 may be defined by the second surface 372, and may extend from the threads 374 to the first surface 370 of the tip 304. The first, second and third ports 382, 384, 386 may each be substantially parallel to the longitudinal axis 368 and may be generally cylindrical shaped.

With the threaded connection, the distance between the first portion 312 of the base 302 and the first end 364 of the tip 304 can be adjusted by simply rotating the tip 304 about the second portion 314 of the base 302. Stated differently, with the threaded connection, the overall length of the modular link assembly 300 can be adjusted by simply rotating the tip 304 about the second potion 314 of the base 302. Rotation of the tip 304 about the second portion 314 of the base 302 may also serve to open or close the ports 382, 384, 386 formed by the cooperation of the grooves 376, 378, 380 with the grooves 350, 352, 354.

Figure 14D:
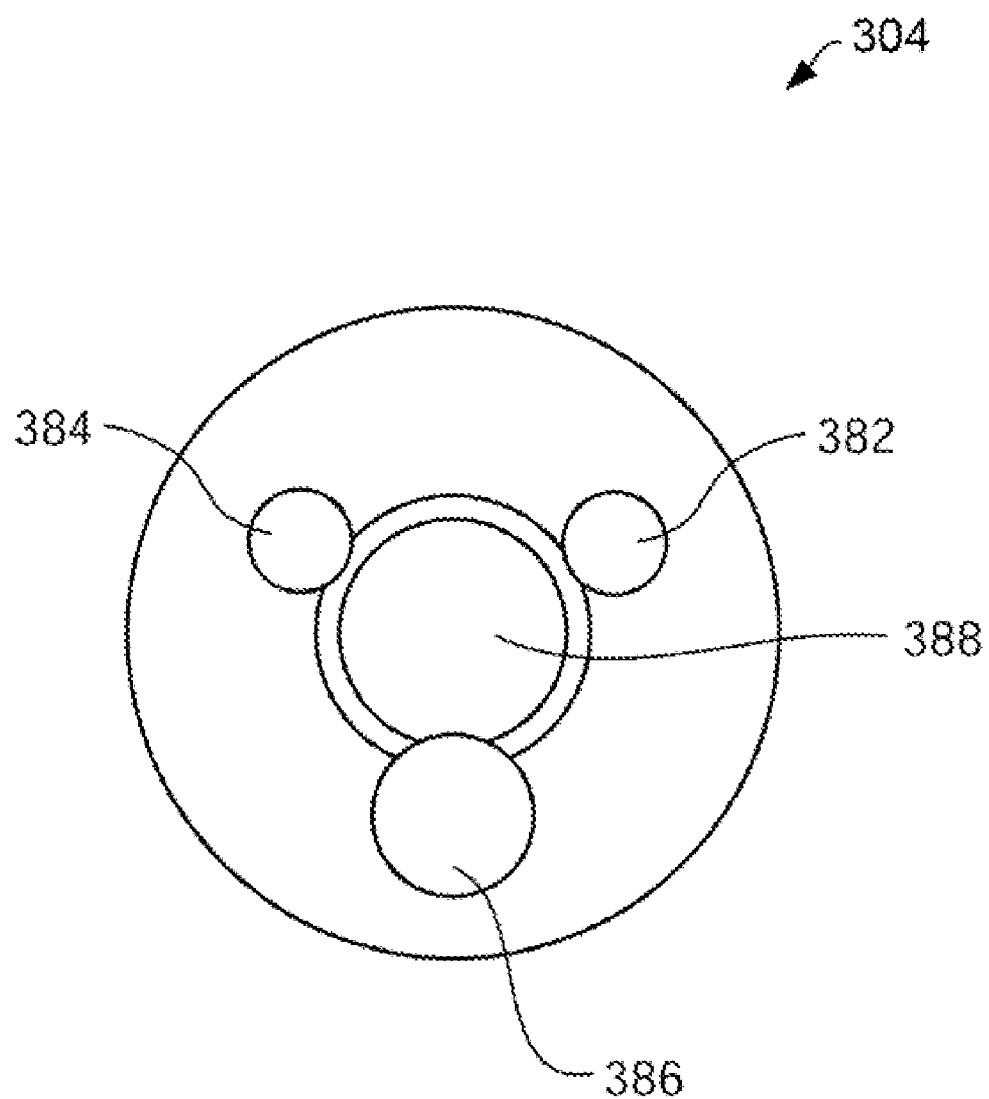

As shown in FIG. 14D, the first, second and third ports 382, 384, 386 may be evenly spaced about the longitudinal axis 368 of the tip 304. The size of each of the ports 382, 384, 386 may identical to one another or may be different from one another. For example, according to various embodiments, the first and second ports 382, 384 are configured as cylinders having diameters on the order of approximately 1.50 millimeters, and the third port 386 is configured as a cylinder having a diameter on the order of approximately 2.50 millimeters. As shown in FIG. 14A, the generally conical shape of the tip 304 operates to "remove" a portion of each "cylinder" proximate the second end 366 of the tip 304. The first, second and third ports 382, 384, 386 are each configured to receive and surround any of a variety of tools or instruments (e.g. ablation tools) which may pass from the first end 24 of the multi-linked device 10 toward the second end 26 of the multi-linked device 10.

The second surface 372 also defines a recess 388 that extends from the first end 364 of the tip 304 toward the second end 366 along the longitudinal axis 368 as shown in FIG. 14C.

According to various embodiments, the recess 388 is generally configured as a complex shape that includes a combination of a first cylinder 390 that extends from the first end 364 toward the second end 366, a second cylinder 392 that extends from the first cylinder 392 toward the second end 366. The complex shape may further include a cone 394 that extends from the second cylinder 392 toward the second end 366 of the tip 304.

As described hereinabove, according to various embodiments, the tip 304 and base 302 may be structured and arranged such that the tip 304 is connected to the base 302 via a snap-fit connection or other type of connection. For embodiments utilizing a snap-fit connection, the tip 304 may still be rotated about the second portion 314 of the base 302, and rotation of the tip 304 may still serve to open or close the ports 382, 384, 386. Regardless of the type of connection, the movement of the tip 304 in both luminal spaces and intracavity spaces may be controlled by controlling the movement of the base 302 when the tip 304 is connected to the base 302. As described hereinabove, the movement of the base 302 may be controlled by controlling the tension placed on each of the cables 16, 18, 20 coupled to the base 302.

Figure 15:
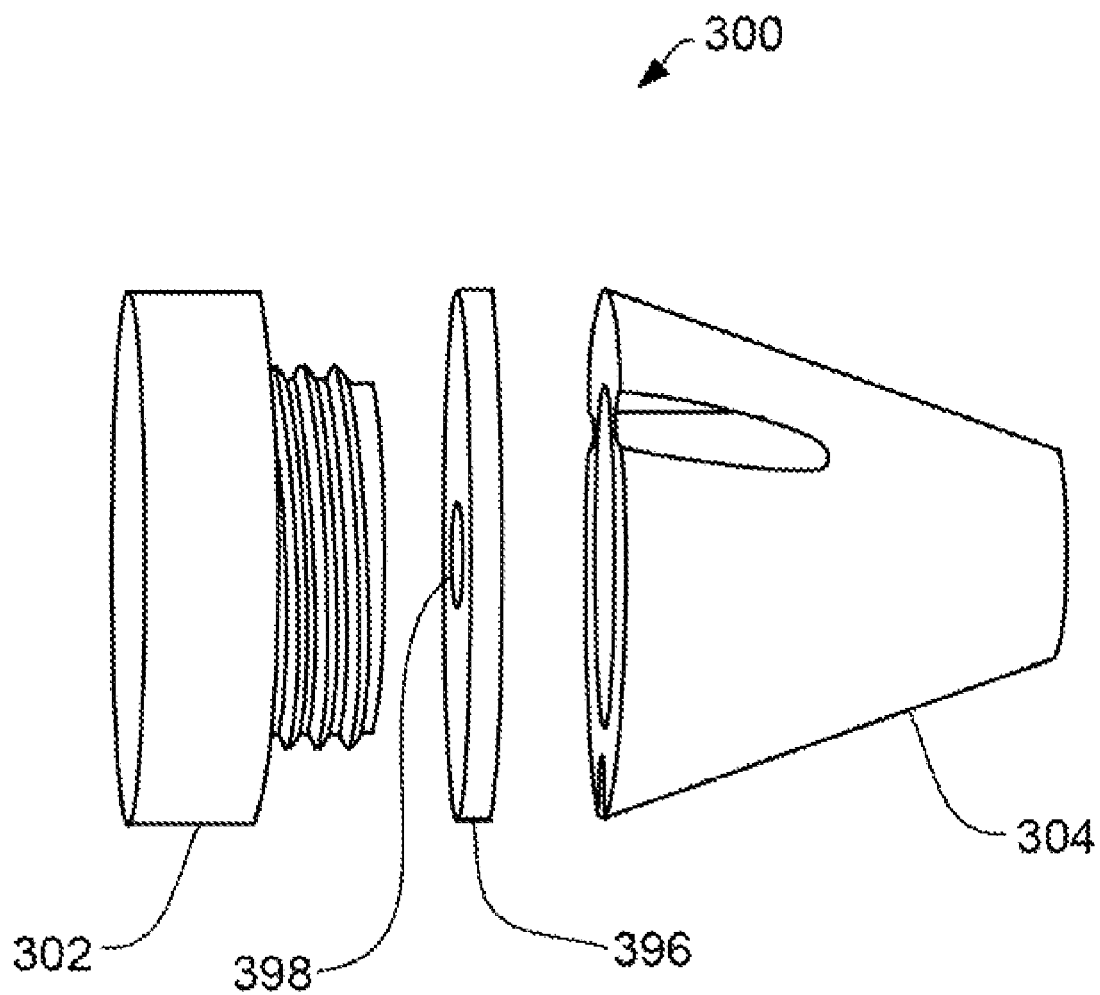
FIG. 15 illustrates various embodiments of a modular link assembly for a multi-linked device.

As shown in FIG. 15, the modular link assembly 300 may also include a printed circuit board 396. For purposes of clarity, the components of the modular link assembly 300 are shown in an exploded view. The printed circuit board 396 defines an opening 398 which allows the printed circuit board 396 to partially or fully surround the second portion 314 of the base 302. According to various embodiments, the opening 398 is a threaded opening, and the printed circuit board 396 may be threadedly connected to the base 302. For such embodiments, the printed circuit board 396 may define first, second and third grooves (not shown for purposes of clarity) which may be respectively aligned with the first, second and third grooves 350, 352, 354 of the base 302 when the printed circuit board 396 is threadedly connected to the base 302. The grooves defined by the printed circuit board 396 may cooperate with grooves 350, 352, 354 of the second portion 314 of the base 302 to form portions of first, second and third ports 382, 384, 386 which are respectively aligned with the first, second and third ports 334, 336, 338 of the first portion 312 of the base 302.

According to other embodiments, the opening 398 may be configured to allow the printed circuit board 396 to be slid into position between the base 302 and the tip 304. For such embodiments, the printed circuit board 396 may be structured and arranged in any suitable shape. For example, for such embodiments, the printed circuit board 396 may be configured in the shape of a closed ring, an open ring, a horseshoe, etc.

The position of the printed circuit board 396 between the base 302 and the tip 304 may be maintained in any suitable manner. For example, according to various embodiments, the second portion 314 of the base 302 and the opening 398 of the printed circuit board 396 may cooperate to constrain lateral movement of the printed circuit board 396. Axial movement of the printed circuit board 396 may be constrained, for example, by the threaded connection between the base 302 and the printed circuit board 396, and/or by the connection (threaded, snap-fit, etc.) between the tip 304 and the base 302.

According to various embodiments, the tip 304 may further include an electronic device and the printed circuit board 396 may serve as the point of attachment for such a device. The electronic device may be embodied as, for example, a light emitting diode, an imaging device (e.g., a camera, an ultrasonic probe, etc.), a solenoid, a piezoelectric device, a sensor (e.g., a MEMS biosensor), etc. Power may be delivered to the printed circuit board 396 in any suitable manner. For example, according to various embodiments, at least two conductors connected to an external power source (e.g., a feeder which actuates movements of the steerable multi-linked device 10) may be run from the proximal end of the multi-linked device 10 to the printed circuit board 396 via the three-dimensional space 240 that exists between the first mechanism 12 and the second mechanism 14 when the first mechanism 12 is received by the second mechanism 14. In other embodiments, the conductors may be run from the proximal end of the multi-linked device 10 to the printed circuit board 396 via one of the working ports.

While several embodiments of the invention have been described herein by way of example, those skilled in the art will appreciate that various modifications, alterations, and adaptions to the described embodiments may be realized without departing from the spirit and scope of the invention defined by the appended claims.

What is claimed is:

1. A system comprising:
a first multi-linked mechanism comprising a plurality of first links;
a second multi-linked mechanism comprising a plurality of second links, wherein at least two of the second links are configured to surround at least two of the first links;
a modular link assembly positioned at an end of at least one of the first multi-linked mechanism or the second multi-linked mechanism, wherein the modular link assembly comprises a base;
a first tip configured to attach to the base; and
a second tip configured to attach to the base.

2. The system of claim 1, wherein the base comprises a plurality of threads.

3. The system of claim 1, wherein at least one of the first tip and the second tip comprise a plurality of threads.

4. The system of claim 1, further comprising a printed circuit board, wherein the printed circuit board is configured to attach to the base.

5. The system of claim 4, wherein at least one of the first tip and the second tip is configured to attach to the base such that the printed circuit board is positioned between the base and the at least one of the first tip and the second tip.

6. The system of claim 4, further comprising at least one electronic device configured to attach to at least one of the first tip and the second tip via the printed circuit board.

7. The system of claim 6, wherein the electronic device comprises one or more of:
a light emitting diode;
a solenoid;
a piezoelectronic device;
a sensor; or
an imaging device.

8. The system of claim 1, wherein:
the modular link assembly is positioned at an end of the first multi-linked mechanism,
the first multi-linked mechanism defines at least one working port along a length thereof,
the base and the first tip are configured to cooperate to define at least a portion of the at least one working port.

9. The system of claim 1, wherein:
the modular link assembly is positioned at an end of the first multi-linked mechanism,
the first multi-linked mechanism defines at least one working port along a length thereof,
the base and the second tip are configured to cooperate to define at least a portion of the at least one working port.

10. The system of claim 1, wherein:
the modular link assembly is positioned at an end of the second multi-linked mechanism,
the second multi-linked mechanism defines at least one working port along a length thereof,
the base and the first tip are configured to cooperate to define at least a portion of the at least one working port.

11. The system of claim 1, wherein:
the modular link assembly is positioned at an end of the second multi-linked mechanism,
the second multi-linked mechanism defines at least one working port along a length thereof,
the base and the second tip are configured to cooperate to define at least a portion of the at least one working port.

12. The system of claim 1, wherein the base defines a passage extending from a first end of the base toward a second end of the base along a longitudinal axis of the base.

13. A system comprising:
a first multi-linked mechanism comprising a plurality of first links;
a second multi-linked mechanism comprising a plurality of second links, wherein at least two of the second links are configured to surround at least two of the first links;
a modular link assembly releasably attached to an end of the first multi-linked mechanism, wherein the modular link assembly comprises a base;
a first tip configured to attach to the base; and
a second tip configured to attach to the base.

14. The system of claim 13, wherein:
the first multi-linked mechanism defines at least one working port along a length thereof,
the base and the first tip are configured to cooperate to define at least a portion of the at least one working port.

15. The system of claim 13, wherein:
the first multi-linked mechanism defines at least one working port along a length thereof,
the base and the second tip are configured to cooperate to define at least a portion of the at least one working port.

16. The system of claim 13, wherein:
the base comprises a first plurality of threads,
at least one of the first tip and the second tip comprise a second plurality of threads.

17. A system comprising:
a first multi-linked mechanism comprising a plurality of first links;
a second multi-linked mechanism comprising a plurality of second links, wherein at least two of the second links are configured to surround at least two of the first links;
a modular link assembly releasably attached to an end of the second multi-linked mechanism, wherein the modular link assembly comprises a base;
a first tip configured to attach to the base; and
a second tip configured to attach to the base.

18. The system of claim 17, wherein:
the second multi-linked mechanism defines at least one working port along a length thereof,
the base and the first tip are configured to cooperate to define at least a portion of the at least one working port.

19. The system of claim 17, wherein:
the second multi-linked mechanism defines at least one working port along a length thereof,
the base and the second tip are configured to cooperate to define at least a portion of the at least one working port.

20. The system of claim 17, wherein:
the base comprises a first plurality of threads,
at least one of the first tip and the second tip comprise a second plurality of threads.

* * * * *